(12) United States Patent
Bunschoten et al.

(10) Patent No.: US 8,048,869 B2
(45) Date of Patent: Nov. 1, 2011

(54) PHARMACEUTICAL COMPOSITION FOR USE IN HORMONE REPLACEMENT THERAPY

(75) Inventors: Evert Johannes Bunschoten, Heesch (NL); Herman Jan Tijmen Coelingh Bennink, Driebergen (NL); Christian Franz Holinka, New York, NY (US)

(73) Assignee: Pantarhei Bioscience B.V. (NL)

( * ) Notice: Subject to any disclaimer, the term of this patent is extended or adjusted under 35 U.S.C. 154(b) by 1093 days.

(21) Appl. No.: 10/478,262

(22) PCT Filed: May 17, 2002

(86) PCT No.: PCT/NL02/00317
§ 371 (c)(1),
(2), (4) Date: May 25, 2004

(87) PCT Pub. No.: WO02/094276
PCT Pub. Date: Nov. 28, 2002

(65) Prior Publication Data
US 2004/0198671 A1    Oct. 7, 2004

(30) Foreign Application Priority Data

| May 18, 2001 | (EP) | 01201896 |
| May 23, 2001 | (EP) | 01201945 |
| May 23, 2001 | (EP) | 01201946 |
| May 23, 2001 | (EP) | 01201947 |
| Aug. 31, 2001 | (EP) | 01203305 |
| Nov. 15, 2001 | (EP) | 01204377 |
| Feb. 21, 2002 | (EP) | 02075695 |

(51) Int. Cl.
*A61K 31/56* (2006.01)

(52) U.S. Cl. .................... 514/171; 514/182
(58) Field of Classification Search .......... 514/182, 514/171
See application file for complete search history.

(56) References Cited

U.S. PATENT DOCUMENTS

| 3,440,320 A | 4/1969 | Sackler et al. |
| 3,797,494 A * | 3/1974 | Zaffaroni |
| 4,460,372 A * | 7/1984 | Campbell et al. |
| 4,573,996 A * | 3/1986 | Kwiatek et al. |
| 4,624,665 A * | 11/1986 | Nuwayser |
| 4,722,941 A * | 2/1988 | Eckert et al. |
| 4,762,717 A * | 8/1988 | Crowley, Jr. |
| 4,937,238 A | 6/1990 | Lemon |
| 5,063,507 A | 11/1991 | Lindsey et al. |
| 5,130,137 A * | 7/1992 | Crowley, Jr. |
| 5,211,952 A * | 5/1993 | Spicer et al. |
| 5,223,261 A * | 6/1993 | Nelson et al. |
| 5,340,584 A * | 8/1994 | Spicer et al. |
| 5,340,585 A * | 8/1994 | Pike et al. |
| 5,340,586 A * | 8/1994 | Pike et al. |
| 5,468,736 A * | 11/1995 | Hodgen |
| 5,633,242 A | 5/1997 | Oettel et al. |
| 5,662,927 A | 9/1997 | Ehrlich et al. |
| 5,827,843 A | 10/1998 | Koninckx |
| 6,214,815 B1 | 4/2001 | Shangold et al. |
| 6,500,814 B1 | 12/2002 | Hesch |
| 2002/0183299 A1 | 12/2002 | Voskuhl |

FOREIGN PATENT DOCUMENTS

| DE | 23 36 433 A | * | 4/1975 |
| DE | 23 36 434 A | * | 4/1975 |
| DE | 24 26 779 A | * | 12/1975 |
| DE | 19917930 A1 | | 10/2000 |
| EP | 0402950 A | | 12/1975 |
| EP | 468690 A1 | | 7/1991 |
| EP | 1700602 A1 | | 5/2001 |
| WO | WO 96 03929 A | * | 2/1966 |
| WO | 9218107 A1 | | 10/1992 |
| WO | 9426207 | | 11/1994 |

(Continued)

OTHER PUBLICATIONS

Ullom-Minnich, Am Fam Physician 1999;60:194-202.*

(Continued)

*Primary Examiner* — San-Ming Hui
(74) *Attorney, Agent, or Firm* — The Webb Law Firm

(57) ABSTRACT

One aspect of the invention is concerned with a method of hormone replacement therapy, which method comprises administering to a person in need of such a therapy an effective amount of an estrogenic component selected from the group consisting of: substances represented by the formula

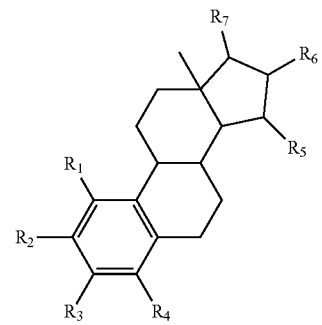

in which formula $R_1$, $R_2$, $R_3$, $R_4$ independently are a hydrogen atom, a hydroxyl group or an alokxy group with 1-5 carbon atoms; each of $R_5$, $R_6$, $R_7$ is a hydroxyl group; and no more than 3 of $R_1$, $R_2$, $R_3$, $R_4$ are hydrogen atoms; precursors capable of liberating a substance according to the aforementioned formula when used in the present method, and mixtures thereof; said composition containing virtually no progestogen or anti-progestin.

Another aspect of the invention relates to a drug delivery system for enteral or parenteral administration that contains at least 1 μg of the aforementioned estrogenic component and virtually no progestogen or anti-progestin.

40 Claims, 6 Drawing Sheets

FOREIGN PATENT DOCUMENTS

| | | |
|---|---|---|
| WO | 9502408 A1 | 1/1995 |
| WO | 9517895 | 7/1995 |
| WO | 9858657 A1 | 12/1998 |
| WO | 0062753 | 10/2000 |
| WO | 0073416 A1 | 12/2000 |
| WO | 0130357 A | 5/2001 |
| WO | 0185154 A2 | 11/2001 |

OTHER PUBLICATIONS

H. Seeger, et al., "The Inhibitory Effect of Endogenous Estrogen Metabolites on Copper-Mediated in Vitro Oxidation of LDL," International Journal of Clinical Pharmacology and Therapeutics. Germany Jul. 1998, vol. 36, No. 7, Jul. 1998, pp. 383-385.

C. F. Holinka et al., "In-Vivo Effects of Estetrol on the Immature Rat Uterus," Biology of Reproduction, vol. 20, No. 2, 1979, pp. 242-246.

C. F. Holinka et al., "Comparison of Effects of Estetrol and Tamoxifen With Those of Estriol and Estradiol on the Immature Rat Uterus," Biology of Reproduction, vol. 22, No. 4, 1980, pp. 913-926.

Visser et al., "In vitro effects of estetrol on receptor binding, drug targets and human liver cell metabolism," Climacteric (2008) 11(1) Appx. II: 1-5.

Visser et al., "First human exposure to exogenous single-dose oral estetrol in early postmenopausal women," Climacteric (2008) 11(1): 1-10.

Visser et al., "Clinical applications of estetrol," J. Of Steroid Biochem and Molecular Biol. (2009) 114: 85-89.

Holinka et al., "Estetrol: A unique steroid in human pregnancy," J. of Steroid Biochem and Molecular Biol. (2009) 110: 138-143.

Coelingh Bennink et al., "Oral bioavailability and bone sparing effects of estetrol in an osteoporosis model," Climacteric (2008) 11 (Supp 3): 1-13.

Albertazzi Paola et al., "The Effect of Tibolone Versus Continuous Combined Norethisterone Acetate and Oestradiol on Memory, Libido and Mood of Postmenopausal Women: A Pilot study"; Database Biosis 'Onlinel; Oct. 31, 2000; pp. 223-229; vol. 36, No. 3; Biosciences Information Service, Philadelphia, PA., U.S.

Allen et al., An Ovarian Hormone: Preliminary Report on Its Localization, Extraction and Partial Purification, and Action in Test Animals, JAMA, Sep. 8, 1923, vol. 81, pp. 819-821.

Allen et al., The Induction of a Sexually Mature Condition in Immature Females by Injection of the Ovarian Follicular Hormone, Am. J. Physiol., 1924, vol. 69, pp. 577-588.

Jones et al., The Effects of Various Steroids on the Vaginal Histology in the Rat, Fertility and Sterility, Apr. 1973, vol. 24, No. 4, pp. 284-291.

Tulchinsky et al., Plasma Esterol as an Index of Fetal Well-Being, J. Clin. Endocrinol. Metab., 1975, vol. 40. pp. 560-567.

Jozan et al., Different Effects of Oestradiol, Oestriol, Oestrol and of Oestrone on Human Breast Cancer Cells (MCF-7) in Long Term Tissue Culture, Acta Endocrinologica, 1981, vol. 98, pp. 73-80.

Hammond et al., A Versatile Method for the Determination of Serum Cortisol Binding Globulin and Sex Hormone Binding Globulin Binding Capacities, 1983, vol. 132, pp. 101-110.

Elger et al., Sulfamates of Various Estrogens are Prodrugs with Increased Systemic and Reduced Hepatic Estrogenicity at Oral Application, J. Steroid Biochem. Molec. Biol., 1995, vol. 55, No. 3 / 4, pp. 395-403.

Murphy et al., Endometrial Effects of Long-Term Low-Dose Administration of RU486, Fertility and Sterility, Apr. 1995, vol. 63, No. 4, pp. 761-766.

Reel et al., Survey and Assessment of Mammalian Estrogen Biological Assays for Hazard Characterization, Fundamental and Applied Toxicology, 1996, vol. 34, pp. 288-305.

Beral et al., Use of HRT and the Subsequent Risk of Cancer, Journal of Epidemiology and Biostatistics, 1999, vol. 4, No. 3, pp. 191-215.

Tavani et al., The Adverse Effects of Hormone Replacement Therapy, Drugs & Aging, May 1999, vol. 14, No. 5, pp. 347-357.

Pike et al., Progestins and Menopause: Epidemiological Studies of Risks of Endometrial and Breast Cancer, Steroids, 2000, vol. 65, pp. 359-664.

Avvakumov et al., Steroid-binding Specificity of Human Sex Hormon-binding Globulin Is Influenced by Occupancy of a Zinc-binding Site, The Journal of Biological Chemistry, Aug. 25, 2000, vol. 275, No. 34, pp. 25920-25925.

Jansson et al., "Estrogen Induces a Potent Suppression of Experimental Autoimmune Encephalomyelitis and Collagen-Induced Arthritis in Mice", Journal of Neuroimmunology, Elsevier Science Publishers BV XX, 1994, vol. 53, No. 2, pp. 203-207.

Erdbruegger et al., Drug Discovery Today: Disease Mechanisms (2004), vol. 1, pp. 73-81.

Lab Tests Online (www.labtestsonline.org/understanding/conditions/autoimmune.html) retrieved on Oct. 15, 2009.

www.tiscali.co.uk/lifestyle/healthfitness/health_advice/netdoctor/archive/000489.html, retrieved on Oct. 15, 2009.

MedlinePlus Medical Encyclopedia: Mutiple Sclerosis, retrieved on Mar. 28, 2008 via www.nlm.nih.gov/medlineplus/ency/article/000737.htm, dated on Aug. 6, 2007, p. 1 and 2; also see WebMD: Multiple Sclerosis—Prevention, retrieved on Mar. 28, 2008 via www.webmd.com/multiple-sclerosis/tc/multiple-sclerosis-ms-prevention, dated on Mar. 23, 2006.

MedlinePlus Medical Encyclopedia: rheumatoid arthritis, retrieved on Mar. 28, 2008 via www.nlm.nih.gov/medlineplus/ency/article/000431.htm, dated on Jul. 27, 2007, p. 1-2 and 4; also WebMD: Rheumatoid Arthritis—Prevention, retrieved on Mar. 28, 2008 via www.webmd.com/rheumatoid-arthritis/tc/rheumatoid-arthritis-prevention, dated on Aug. 23, 2006.

Mueck et al., "Angio and Anti-Angiogenetic Effects of Estradiol and its Metabolites", J. Clin. Basic Cardiol., 2001, pp. 153-155, vol. 4, No. 2.

Shah et al., "Estrogen and Skin. An Overview", Am. J. Clin. Dermatol., 2001, pp. 143-150, vol. 2, No. 3.

Sitruk-Ware et al., "Local Hormonal Treatment for Urogenital Atrophy After Menopause", Shweiz. Rundsch, Med. Praxis, 1997, pp. 1245-1248, vol. 86, No. 33; and Sitruk-Ware, English Translation, 1997. Praxis, Schweirzerische Rundschau fur Medizin, vol. 86, No. 33, pp. 1-13.

Schmidt et al., "Treatment of Skin Aging with Topical Estrogens", Int. J. Dermatol., 1996, pp. 669-674, vol. 35, No. 9.

Younglai et al., Journal of Clinical Endocrinology and Metabolism, 1968, vol. 28, Issue 11, pp. 1611-1617.

Webster Ninth New Collegiate Dictionary, 2000, Definition of Prevention, p. 1.

Willhite et al., Pharmacotherapy, 2001, vol. 21, Issue 4, pp. 464-480.

Tseng et al., "Heterogeneity of Saturable Estradiol Binding Sites in Nuclei of Human Endometrium. Estetrol Studies", (1978), vol. 9, pp. 1145-1148.

Fishman et al., "Fate of 15 α-Hydroxyestriol-3H in Adult Man", J. Clin. Endocrinol. Metab., (1970), vol. 31, pp. 436-438.

Levine et al., "Uterine vascular effects of estetrol in nonpregnant ewes", Am. J. Obstet. Gynecol., (1984), [148], vol. 73, pp. 735-738.

Martucci et al., "Direction of Estradiol Metabolish as a Control of its Hormonal Action—Uterotrophic Activity of Estradiol Metabolites", Endocrin., (1977), vol. 101, pp. 1709-1715.

Martucci et al., "Uterine Estrogen Receptor Binding of Catecholestrogens and of Estetrol (1,3,5(10)-Estratriene-3, 15a, 16a, 17 β-Tetrol)", Steroids, (1976), vol. 27, pp. 325-333.

Tseng et al., "Competition of Estetrol and Ethynylestradiol with Estradiol for Nuclear Binding in Human Endometrium", Journal of Steroid Biochemistry, (1976), vol. 7, pp. 817-822.

Kuipers et al., "Enterohepatic Circulation in the Rat", Gastroenterol., vol. 88, pp. 403-411 (1985).

Schwartz, "A Model for the Regulation of Ovulation in the Rat", Recent Prog. Horm. Res., vol. 25, pp. 1-55, (1969).

Beattie et al., "The Differential Effects of Diestrous Progestogen Administration on Proestrous Gonadotrophin Levels, Endocrinol", vol. 97, pp. 885-890, (1975).

De Visser et al., Endocrinological Studies with (7a, 17 a)-17-Hydroxy-7-me norpregn-5(10)-en-20-yn-3-one (Org OD 14), Arzneim, Forsh., vol. 34, pp. 1010-1020, (1984).

National Cancer Institute: Breast cancer prevention retrieved online Aug. 7, 2007 from the internet; http://www.cancer.gov/templates/doc.aspx?viewed=D972A74B-D25A-4F86-B8ED-33EB3C0450E4&version, p. 1.

Medline Plus: Medical Encyclopedia: Ovarian cancer retrieved online on Aug. 9, 2007 from the internet: https://www.nlm.nih.gov/medlineplus/ovariancancer.html, p. 1 dated Jul. 31, 2007.

Coelingh-Bennink et al., "Estetrol review: profile and potential clinical applications", International Menopause Society, Climateric, vol. 11, (Suppl 1), pp. 47-58 (2008).

Speroff et al., Clinical Gynecologic Endocrinology and Infertility, Seventh Edition, p. 270 (partial), 2004.

White et al., "The pharmacokinetics of Intravenous Estradiol: A Preliminary Study", Pharmacotherapy, vol. 18, pp. 1343-1346, (1998) (Abstract).

Hammond et al., "Estetrol does not bind sex hormone binding globulin or increase its production by human HepG2 cells", International Menopause Society, Climateric, vol. 11, (Suppl. 1), pp. 41-46, (2008).

National Institute of Child Health and Human Development, NIH Publication No. 02-2413 retrieved online on Aug. 9, 2007.

Breast Cancer Prevention retrieved online Aug. 7, 2007 from the internet; http://www.cancer.gov/cancertopics/pdq/prevention/breast/Patient/page 3.

Prophylactic definition—Medical Dictionary of Popular Medical Terms; retrieved on Mar. 14, 2008 via www.medterms.com/script/main/art.asp?articlekey=11902.

Zips et al., in vivo, 2005, vol. 19, pp. 1-8.

Holinka et al., Biology of Reproduction, 1980, vol. 22, pp. 913-926.

Martucci et al., "Impact of Continuously Administered Catechol Estrogens on Uterine Growth and Luteinizing Hormone Secretion", Endocrinology (Dec. 1979), vol. 105, No. 6, pp. 1288-1292.

Weigert et al., "Comparison of Stimulation with Clomiphenes Citrate in Combination with Recombinant Follicle Stimulating Hormone and Recombinant Luteinizing Hormone to Stimulation with a Gonadotropin-Releasing Hormone Agonist Protocol: A Prospective Randomized Study", Fertility and Sterility, (Jul. 2002), vol. 78, No. 1, pp. 34-39.

Trotter et al., "Effects of Postnatal Estradiol and Progesterone Replacement in Extremely Preterm Infants", J. Clin. Endocrinol Metab., (Dec. 1999), vol. 84, No. 12, pp. 4531-4535.

Shanklin et al., "Aqueous Estrogens in the Management of Respiratory Distress SYndrome", J. Reprod. Med. (Aug. 1970), vol. 5, No. 2, pp. 53-71.

Chemical Abstracts Service, Columbus Ohio, US: Jakowicki, "Evaluation of Estriol Level in the Amniotic Fluid in Prolonged Pregnancy", XP002458625, 1979.

Gorwill et al., "Unconjugated Serum Oestriol Levels in Mother and Baby with Meconium Staining of the Amniotic Fluid", Br. J. Obstet. Gynaecol. (Aug. 1978), vol. 85, No. 8, pp. 602-604.

Fogary, Jr., "Postmaturity", J. Am. Osteopath. Assoc., (Jan. 1976), vol. 75, No. 5, pp. 512-517.

Office Action mailed on Nov. 18, 2008 in U.S. Appl. No. 10/478,264.
Office Action mailed on May 22, 2009 in U.S. Appl. No. 10/478,264.
Office Action mailed on Mar. 17, 2008 in U.S. Appl. No. 10/478,357.
Office Action mailed on May 16, 2008 in U.S. Appl. No. 10/478,357.
Office Action mailed on Dec. 16, 2008 in U.S. Appl. No. 10/478,357.
Office Action mailed on May 28, 2009 in U.S. Appl. No. 10/478,357.
Office Action mailed on Apr. 6, 2007 in U.S. Appl. No. 10/478,365.
Office Action mailed on Sep. 7, 2007 in U.S. Appl. No. 10/478,365.
Office Action mailed on Apr. 1, 2008 in U.S. Appl. No. 10/478,365.
Office Action mailed on Jun. 8, 2009 in U.S. Appl. No. 10/478,365.
Office Action mailed on Jan. 24, 2007 in U.S. Appl. No. 10/495,707.
Office Action mailed on Dec. 28, 2007 in U.S. Appl. No. 10/495,707.
Office Action mailed on Aug. 19, 2008 in U.S. Appl. No. 10/495,707.
Office Action mailed on May 22, 2009 in U.S. Appl. No. 10/495,707.
Office Action mailed on Oct. 15, 2007 in U.S. Appl. No. 10/517,509.
Office Action mailed on Dec. 19, 2007 in U.S. Appl. No. 10/517,509.
Office Action mailed on Mar. 26, 2008 in U.S. Appl. No. 10/517,509.
Office Action mailed on Jan. 5, 2009 in U.S. Appl. No. 10/517,509.
Office Action mailed on Aug. 18, 2009 in U.S. Appl. No. 10/517,509.
Office Action mailed on Apr. 3, 2007 in U.S. Appl. No. 10/517,686.
Office Action mailed on Aug. 9, 2007 in U.S. Appl. No. 10/517,686.
Office Action mailed on Apr. 4, 2008 in U.S. Appl. No. 10/517,686.
Office Action mailed on May 29, 2009 in U.S. Appl. No. 10/517,686.
Office Action mailed on Apr. 23, 2007 in U.S. Appl. No. 10/521,040.
Office Action mailed on Aug. 17, 2007 in U.S. Appl. No. 10/521,040.
Office Action mailed on Apr. 2, 2008 in U.S. Appl. No. 10/521,040.
Office Action mailed on Jun. 1, 2009 in U.S. Appl. No. 10/521,040.

* cited by examiner

PHARMACEUTICAL COMPOSITION FOR USE IN HORMONE REPLACEMENT THERAPY

TECHNICAL FIELD OF THE INVENTION

The present invention is concerned with a method of hormone replacement therapy. More particularly, the present invention is concerned with a method of hormone replacement therapy that comprises the administration, to a person in need of such a therapy, of an effective amount of an estrogenic component.

BACKGROUND OF THE INVENTION

In hormone replacement therapy (HRT), sometimes also referred to as estrogen replacement therapy, estrogens are administered to prevent or treat symptoms resulting from estrogen deficiency or hypoestrogenism. Hypoestrogenism can occur in both females and males, and can lead to disorders and ailments such as osteoporosis (loss of bone mass), arteriosclerosis, climacteric symptoms such as hot flushes (flashes), sweats, urogenital atrophy, mood disturbances, insomnia, palpitations. Estrogen deficiency has also been associated with cognitive disturbances and Alzheimer's disease.

Hypoestrogenism, and in particular chronic hypoestrogenism, is frequently observed in (peri-)menopausal and post-menopausal women. However, it can also result from hypogonadism or castration, as well as from primary ovarian failure, treatment of e.g. breast cancer with aromatase inhibitor and gonadotropin-releasing hormone analogue treatment of benign gynaecological diseases such as endometriosis, adenomyosis, uterine fibroids (leiomyomas), dysmenorrhoea, menorrhagia and metrorrhagia.

Endogenous and exogenous estrogens fulfil important central nervous and metabolic functions in the female organism: normal estrogen levels make a decisive contribution to a woman's well-being. Notwithstanding the widespread use of estrogens in HRT methods, there are still some unsolved problems. Well-known estrogens, in particular biogenic estrogens (i.e. estrogens that occur naturally in the human body), are eliminated from the blood stream very quickly. For instance, for the main human biogenic estrogen 17β-estradiol the half-life is around 1 hour. As a result, between separate administration events, blood serum levels of such biogenic estrogens tend to fluctuate considerably. Thus, shortly after administration the serum concentration is usually several times higher than the optimum concentration. In addition, if the next administration event is delayed, serum concentrations will quickly decrease to a level where the estrogen is no longer physiologically active.

The most important synthetically altered estrogenic steroid is 17α-ethinyl estradiol (EE). This estrogen is dominant in oral hormonal contraception. Apart from EE, mestranol has been used in a few cases; mestranol is a "prodrug" that is metabolised to EE in the organism. The liver is a target organ for estrogens. The secretion activity that is affected by estrogens in the human liver includes increased synthesis of transport proteins CBG, SHBG, TBG, several factors that are important for the physiology of blood clotting, and lipoproteins. The strong hepatic estrogenicity of ethinyl estradiol and diethylstilbestrol (DES), especially their effect on haemostasis factors, may explain why these synthetic estrogens have been associated with the enhanced risk of thromboembolism. Other undesirable 'side-effects that have been reported in relation to the use of synthetic estrogens include fluid retention, nausea, bloating, cholelithiasis, headache, breast pain and an enhanced risk of breast cancer with longer term usage. The aforementioned deficits are of considerable clinical significance when commonly known biogenic or synthetic estrogens are applied. Consequently, there is an as yet unmet need for estrogens that do not display these deficits and which can suitably be employed in HRT methods to effectively replace endogenous ovarian secretion of estradiol, i.e. to treat or prevent symptoms of hypoestrogenism.

HRT employs continuous administration of effective amounts of an estrogen for prolonged periods of time. The administration of estrogens has been associated, however, with endometrial proliferation in women and it is now widely accepted that "unopposed" estrogen therapy substantially increases the risk of endometrial cancer (Cushing et al., 1998. Obstet. Gynecol.91, 35-39; Tavani et al., 1999. Drugs Aging, 14, 347-357). There is also evidence of a significant increase in breast cancer with long-term (10-15 years) use of estrogen therapy (Tavani et al., 1999. Drugs Aging, 14, 347-357; Pike et al., 2000. Steroids, 65, 659-664).

In order to counteract the negative effects of unopposed estrogen therapy, adjunctive progestogen treatment is nowadays commonly applied. Regular progestogen administration is believed to inhibit the continual estrogen stimulation of the endometrium through an anti-proliferative effect and appears to reduce the incidence of endometrial carcinoma in post-menopausal women receiving estrogen replacement therapy (Beral et al., 1999. J. Epidemiol. Biostat., 4, 191-210). Such an adjunctive treatment, generally using synthetic progestogens, is given either in continuous combined regimens with estrogen, or added sequentially, typically for about 14 days each month, to continuous estrogen treatment. Sequential regimens are associated with undesirable vaginal bleeding in response to periodic progestogen withdrawal, while continuous combined therapy frequently results in unpredictable breakthrough bleeding. Unacceptable bleeding of this type is the most frequent reason for discontinuation of hormone replacement therapy.

Additional adverse effects of adjunctive progestogens include oedema, abdominal cramps, breast tenderness and mood symptoms (Hahn, 1989. Am. J. Obstet. Gynecol., 161, 1854-1858). Some synthetic progestogens unfavourably affect lipid patterns and thus negate or attenuate the estrogen induced cardioprotective effects (Sitruk-Ware, 2000. Steroids, 65, 651-658).

To avoid the need for adjunctive progestogens, efforts have been made to synthesise molecules with selective estrogenic properties so as to obtain desirable effects in certain target tissues, such as bone, liver, brain and in tissues that mediate cardioprotection, while minimally affecting other tissues, such as endometrium and breast. These efforts were based on the emerging knowledge that the interaction of estrogens with protein regulating estrogen responsiveness, i.e. estrogen receptors, may vary in different target tissues. Estrogenic, compounds, which selectively modulate estrogen receptors in different target tissues and therefore may be expected to have selective estrogen agonistic/antagonistic effects, are known as selective estrogen receptor modulators (SERMs) (Katzenellenbogen et al., 2000. J. Steroid Biochem. Mol. Biol., 74, 279-285; Burger, 2000. Horm. Res., suppl 3, 25-29).

The optimal SERM is expected to affect differentiated cellular functions without inducing proliferation, because enhanced proliferation is associated with increased cancer risk. Regarding the endometrium, exaggerated proliferation (hyperplasia) has been demonstrated to be a precursor of endometrial cancer. Furthermore, the optimal SERM would eliminate the need for adjunctive progestogen treatment and its adverse effects. An example of a synthetic SERM that is commercially available is raloxifene, a benzothiophene antiestrogen (Clemett et al., 2000. Drugs, 60, 379-411). A drawback of the known synthetic SERM's is that these molecules do not occur naturally in the human body and that they bear little resemblance to the estrogen receptor agonists that are found in the human body, e.g. estrogens such as estrone, estradiol and estriol.

It is an objective of the present invention to provide a method of hormone replacement therapy, wherein an estrogenic component is administered which does not display the deficits that have been observed for commonly known biogenic or synthetic estrogens and which estrogenic component exhibits SERM-like properties, so that co-administration of progestogen can be avoided. In addition the present method aims to employ an estogenic component that is biogenic or that closely resembles a biogenic estrogenic substance.

SUMMARY OF THE INVENTION

The inventors have unexpectedly found that these objectives can be realised by employing estrogenic substances that are represented by the following formula

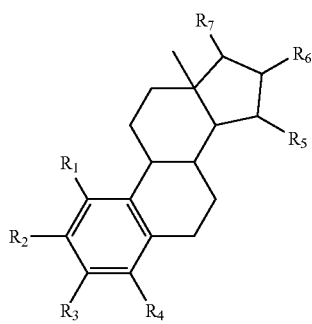

in which formula $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; and no more than 3 of $R_1$, $R_2$, $R_3$, $R_4$ are hydrogen atoms.

These estrogens are different from the estrogens commonly applied in estrogen replacement therapy, i.e. ethinyl estradiol, estradiol and its esters such as the acetate, valerate or benzoate, mestranol, the conjugated equine estrogens and estrone sulfate.

A known representative of this group of estrogenic substances is 1,3,5 (10)-estratrien-3,15α,16α,17β-tetrol, also known by the names of estetrol, oestetrol and 15α-hydroxyestriol. Estetrol is an estrogen that is produced by the fetal liver during human pregnancy. Unconjugated estetrol levels in maternal plasma peak at about 1.2 ng/ml at term pregnancy and are about 12 times higher in fetal than in maternal plasma (Tulchinsky et al., 1975. J. Clin. Endocrinol. Metab., 40, 560-567).

Although the inventors do not wish to be bound by theory, it is believed that the estrogenic component in the pharmaceutical composition according to the present invention interacts with the estrogen receptors in human endometrium in a manner which is clearly different from the interaction observed for those estrogens that are commonly used in hormone replacement therapy. As will be explained below, this phenomenon may well be linked to the selective interaction with the ERα and ERβ estrogen receptors that has been observed for the present estrogenic substances. It is postulated that estetrol functions in a manner similar to a SERM by selectively interacting with the estrogen receptors to achieve estrogenic effects while minimising the classical growth-promoting effects of the aforementioned commonly used estrogens. In comparison to, for instance, estradiol and ethinyl estradiol, the active components according to the present invention display a limited proliferative effect on the endometrium. Thus, unlike what is the case for these other estrogens, there is no need for adjunctive progestogen (or anti-progestogen) treatment, particularly not if the present estrogenic substances are administered in moderate doses. The administration of the estrogenic components according to the invention without supplementary progestogen or anti-progestogen delivers the full benefits of estrogen replacement therapy without the drawbacks associated with the use of the latter hormones.

In 1970, Fishman et al., "Fate of 15α-hydroxyestriol-$^3$H in Adult Man", J Clin Endocrinol Metab (1970) 31, 436-438, reported the results of a study wherein tritiuni labeled 15α-hydroxyestriol (estetrol) was administered intravenously to two adult women. It was found that the estetrol was rapidly and completely excreted in urine as the glucosiduronate and that virtually no metabolism except for conjugation took place.

Between 1975 and 1985 several researchers have investigated the properties of estetrol and reported on its estrogenic potency and uterotrophic activity. The most relevant publications that were issued during this period are mentioned below:

Levine et al., 1984. Uterine vascular effects of estetrol in nonpregnant ewes. Am. J. Obstet. Gynecol., 148:73, 735-738: "When intravenously administered in nonpregnant ewes, estetrol is 15 to 30 times less potent than estriol and 17β-estradiol in uterine vasodilation".

Jozan et al., 1981. Different effects of oestradiol, oestriol, oestetrol and of oestrone on human breast cancer cells (MCF-7) in long term tissue culture. Acta Endocrinologica, 98, 73-80: "Estetrol agonistic potency is 2% of the magnitude observed for 17β-estradiol in in vitro cell proliferation".

Holinka et al., 1980. Comparison of effects of estetrol and tamoxifen with those of estriol and estradiol on the immature rat uterus. Biol. Reprod. 22, 913-926: "Subcutaneously administered estetrol has very weak uterotrophic activity and is considerable less potent than 17β-estradiol and estriol".

Holinka et al., 1979. In vivo effects of estetrol on the immature rat uterus. Biol. Reprod. 20, 242-246: "Subcutaneously administered estetrol has very weak uterotrophic activity and is considerable less potent than 17β-estradiol and estriol".

Tseng et al., 1978. Heterogeneity of saturable estradiol binding sites in nuclei of human endometrium. Estetrol studies. J. Steroid Biochem. 9, 1145-1148: "Relative binding of estetrol to estrogen receptors in the human endometrium is 1.5% of 17β-estradiol".

Martucci et al., 1977. Direction of estradiol metabolism as a control of its hormonal action-uterotrophic activity of estradiol metabolites. Endocrin. 101, 1709-1715: "Continuous administration of estetrol from a subcutaneous depot shows very weak uterotrophic activity and is considerably less potent than 17β-estradiol and estriol".

Tseng et al., 1976. Competition of estetrol and ethynylestradiol with estradiol for nuclear binding in human endometrium. J. Steroid Biochem. 7, 817-822: "The relative binding constant of estetrol binding to the estrogen receptor in the human endometriun is 6.25% compared to 17β-estradiol (100%)".

Martucci et al., 1976. Uterine estrogen receptor binding of catecholestrogens and of estetrol (1,3,5(10)-estratriene-3,15alpha, 16alpha, 17beta-tetrol). Steroids, 27, 325-333: "Relative binding affinity of estetrol to rat uterine cytosol estrogen receptor is 0.5% of 17β-estradiol (100%). Furthermore, the relative binding affinity of estetrol to rat uterine nuclear estrogen receptor is 0.3% of 17β-estradiol (100%)".

All of the above publications have in common that the authors have investigated the estrogenic potency of estetrol. Without exception they all conclude that estetrol is a weak estrogen. In some of the cited articles the estrogenic potency of estetrol has been found to be lower than that of another biogenic estrogen, namely, 17β-estradiol, which is considered to be a relatively weak estrogen (e.g. compared to ethinyl estradiol). With these findings in mind, it is not surprising that the interest in estetrol has dwindled since the early eighties and that no publications on the properties of estetrol have been issued since.

U.S. Pat. No. 5,468,736 (Hodgen) describes a method of hormone replacement therapy involving the administration of estrogen together with an amount of antiprogestin (antiprogestogen), which inhibits estrogen-induced endometrial proliferation in women. In Example 3 the combined use of estetrol and lilopristone is mentioned. No clues are given in the examples as to the mode and frequency of administration or regarding the dosage level employed. A disadvantage associated with the use of antiprogestins (or antiprogestogens), such as lilopristone, is the risk of inducing abnormal endometrial morphology, i.e. cystic hyperplasia, as has been observed in women who received an antiprogestogen treatment against endometriosis (Murphy et al., 1995. Fertil. Steril., 95, 761-766).

U.S. Pat. No. 5,340,586 (Pike et al.) is concerned with compositions and methods which are effective to treat oophorectomized women, wherein an effective amount of an estrogenic composition and an androgenic composition are provided over a period of time. In the US-patent it is stated that natural and synthetic estrogenic compositions that can be used include natural estrogenic hormones and congeners, including but not limited to estradiol, estradiol benzoate, estradiol cypionate, estradiol valerate, estrone, diethylstilbestrol, piperazine estrone sulfate, ethinyl estradiol, mestranol, polyestradiol phosphate, estriol, estriol hemisuccinate, quinestrol, estropipate, pinestrol and estrone potassium sulfate, and furthermore that equine estrogens, such as equilelinin, equilelinin sulfate and estetrol, may also be employed. Except for the exhaustive inventory of known estrogens, no other reference to estetrol (which is erroneously referred to as an equine estrogen) is made in this US-patent.

The same exhaustive list of estrogens is found in the following patents:

U.S. Pat. No. 4,762,717 (Crowley): A contraceptive method comprising the sequential administration of (1) a combination of luteinizing hormone releasing hormone (LHRH) and estrogen and (2) a combination of LHRH and estrogen and progestogen.

U.S. Pat. No. 5,130,137 (Crowley): A method of treating benign ovarian secretory disorder comprising the sequential administration of (1) a combination of luteinizing hormone releasing hormone (LHRH) and estrogen and (2) a combination of LHRH and estrogen and progestogen.

U.S. Pat. No. 5,211,952 (Spicer et al.): A contraceptive method comprising administering a gonadotropin hormone releasing hormone (GnRH) composition in an amount effective to inhibit ovulation and administering estrogen and progestogen to maintain serum levels above a defined minimum level.

U.S. Pat. No. 5,340,584 (Spicer et al.): A method for preventing conception or for treating benign gynaecological disorders comprising administering a GnRH composition for a first period of time in an amount effective to suppress ovarian estrogen and progesterone production, simultaneously administering an estrogenic composition in an amount effective to prevent symptoms of estrogen deficiency and simultaneously administering a progestogen in an amount effective to maintain serum level of said progestogen at a level effective to decrease endometrial cell proliferation.

U.S. Pat. No. 5,340,585 (Pike et al.): A method of treating benign gynaecological disorders in a patient in whom the risk of endometrial stimulation by estrogenic compositions is minimized or absent, comprising administering a GnRH composition in an amount effective to suppress ovarian estrogen and progesterone production and administering an estrogenic composition in an amount effective to prevent symptoms of estrogen deficiency.

WO 00/73416 (Yifang et al.): A method for regulating the fertility of a host, comprising contacting host ovarian cells with a safe and effective amount of a pharmaceutical composition comprising an antisense oligonucleotide that is complementary to the nucleotide sequence of the follicle stimulating hormone (FSH) receptor. The possibility of combined administration of such an antisense oligonucleotide with an estrogenic steroid is mentioned in the application.

The benefits of the present invention may be realised without the co-administration of anti-progestogens, LHRH compositions, GnRH compositions and/or antisense oligonucleotides that is complementary to the nucleotide sequence of the follicle stimulating hormone (FSH) receptor as proposed in the aforementioned patents. Also, the present invention may suitably be applied in individuals who have not been oophorectomized, or in whom the risk of endometrial stimulation by estrogenic compositions is not minimized or absent. Furthermore the present method does not require the use of a slow release formulation as is dictated by most of the aforementioned US-patents.

In view of the low estrogenic potency of the estetrol-like substances that are employed in accordance with the invention, it is surprising that these substances can effectively be used in a method of hormone replacement. Although the inventors do not wish to be bound by theory, it is believed that the unexpected efficacy of enterally or parenterally administered estetrol-like substances results from the combination of unforeseen favourable pharmacokinetic (ADME) and pharmacodynamic properties of these substances.

As regards the pharmacokinetic properties of the present estrogenic substances the inventors have discovered that their in vivo half-life is considerably longer than that of other biogenic estrogens. Thus, even though estetrol and estetrol-like substances have relatively low estrogenic potency, they may effectively be employed in HRT methods because their low potency is compensated for by a relatively high metabolic stability, as demonstrated by a long half-life.

An advantageous property of the present estrogenic substances resides in the fact that sex hormone-binding globulin (SHBG) hardly binds these estrogenic substances, meaning that, in contrast to most known estrogens, serum levels are representative for bio-activity and independent of SHBG levels.

Another important benefit of the present estrogenic substances is derived from their relative insensitivity to interactions with other drugs (drug-drug interactions). It is well known that certain drugs may decrease the effectiveness of estrogens, such as ethinyl estradiol, and other drugs may enhance their activity, resulting in possible increased side-effects. Similarly estrogens may interfere with the metabolism of other drugs. In general, the effect of other drugs on estrogens is due to interference with the absorption, metabolism or excretion of these estrogens, whereas the effect of estrogens on other drugs is due to competition for metabolic pathways.

The clinically most significant group of estrogen-drug interactions occurs with drugs that may induce hepatic microsomal enzymes which may decrease estrogen plasma levels below therapeutic level (for example, anticonvulsant agents; phenytoin, primidone, barbiturates, carbamazepine, ethosuximide, and methosuximide; antituberculous drugs such as rifampin; antifungal drugs such as griseofulvin). The present estrogenic substances are less dependent on up- and downregulation of microsomal liver enzymes (e.g. P450's) and also are less sensitive to competition with other P450 substrates. Similarly, they do not interfere significantly in the metabolism of other drugs.

The conjugates of most estrogens, as formed in the liver, are excreted in the bile and may be broken down by gut bacteria in the colon to liberate the active hormone which can then be reabsorbed (enterohepatic recirculation). There are clinical reports that support the view that enterohepatic recirculation of estrogens decreases in women taking antibiotics such as ampicillin, tetracycline, etc. Conjugated forms of the present estrogenic substances are hardly excreted in the bile, meaning that they are substantially insensitive to drugs that do influence the enterohepatic recirculation of other estrogens.

The above observations serve to explain why the estrogenic substances of the invention hardly suffer from drug-drug interactions and thus produce a very consistent, i.e. predictable, impact. Thus, the efficacy of the estrogenic substances of the invention is highly reliable.

DETAILED DESCRIPTION OF THE INVENTION

Figure 1:
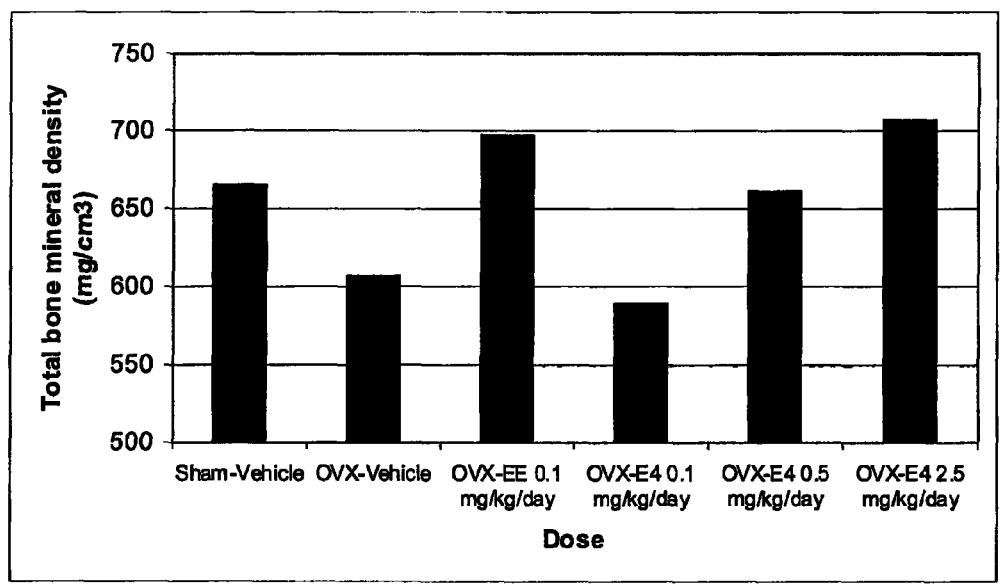
FIG. 1 is a graph showing total bone mineral density from the proximal tibiae of Sham- and OVX-rats orally (po) treated with 17α-ethinyl estradiol (EE), estetrol (E4) or vehicle for 4 consecutive weeks. Data are expressed as the mean values obtained for each group (n=10).

Accordingly, one aspect of the present invention relates to a method of hormone replacement therapy, which method comprises administering to a person in need of such a therapy an effective amount of an estrogenic component selected from the group consisting of:
substances represented by the following formula

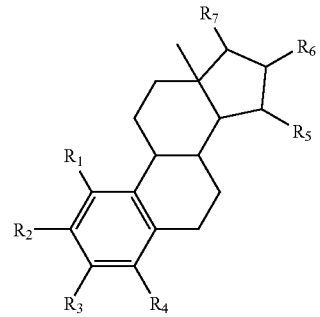

in which formula $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; and no more than 3 of $R_1$, $R_2$, $R_3$, $R_4$ are hydrogen atoms;
precursors capable of liberating a substance according to the aforementioned formula when. used in the present method, and mixtures thereof;
said composition containing virtually no progestogen or antiprogestin.

The HRT method according to the invention may advantageously be used to treat all known forms of hypoestrogenism, e.g. hypoestrogenism associated with (peri-)menopausal and post-menopausal women, hypoestrogenism resulting from hypogonadism or castration, as well as hypoestrogenism resulting from primary ovarian failure, treatment of e.g. breast cancer with aromatase inhibitor and gonadotropin-releasing hormone analogue treatment of e.g. benign gynaecological diseases. Examples of manifestations of hypoestrogenism that can effectively be treated or prevented with the present method in both females and males include osteoporosis, arteriosclerosis, cognitive disturbances and Alzheimer's disease. The method may also advantageously be used in the (prophylactic) treatment of climacteric symptoms such as hot flushes (flashes), sweats, urogenital atrophy, mood disturbances, insomnia and palpitations. The present method is particularly suited for treating or preventing osteoporosis and climacteric symptoms.

The term "estrogenic component" as used throughout this document encompass substances that are capable of triggering an estrogenic response in vivo, as well as precursors that are capable of liberating such an estrogenic component in vivo when used in accordance with the present invention. In order for estrogenic components to trigger such a response they normally have to bind to an estrogen receptor, which receptors are found in various tissues within the mammalian body.

It is noted that the present invention not only encompasses the use of estrogenic components specifically mentioned in this application, but also metabolites of these hormones that display comparable in vivo functionality. In this context it is observed that, for instance, estriol is a metabolite of 17beta-estradiol. The term "estrogenic substances" as used in this document does not encompass tritium ($^3H$) labeled estrogenic substances such as tritium labeled estetrol.

The present estrogenic substances are distinct from both the biogenic and synthetic estrogens that are commonly applied in pharmaceutical formulations in that they contain at least 4 hydroxyl groups. The present substances are special in that the 5 membered ring in the steroid skeleton comprises 3 hydroxyl substituents rather than 0-2.

Known estrogens that contain at least 4-hydroxyl groups and derivatives thereof are:

1, 3, 5(10)-estratrien-2, 3, 15α, 16α, 17β-pentol 2-methyl ether
1, 3, 5(10)-estratrien-2, 3, 15β, 16α, 17β-pentol 2-methyl ether
1, 3, 5(10)-estratrien-2, 3, 16α, 17β-tetrol
1, 3, 5(10)-estratrien-3, 4, 16α, 17β-tetrol 4-methyl ether
1, 3, 5(10)-estratrien-3, 15, 16α, 17β-tetrol
1, 3, 5(10)-estratrien-3, 15α, 16α, 17β-tetrol tetra acetate
1, 3, 5(10)-estratrien-3, 15β, 16β, 17β-tetrol tetra acetate Preferably, the estrogenic substance applied as the active component in the present composition is a so called biogenic estrogen, i.e. an estrogen that occurs naturally in the human body, a precursor of a biogenic estrogen or mixtures thereof. Because biogenic estrogens are naturally present in the fetal and female body, side-effects are not expected to occur, particularly not if the serun levels resulting from the exogenous administration of such estrogens do not substantially exceed naturally occurring concentrations. Since estetrol serum levels in the fetus are several times higher than those found in pregnant females and knowing that the fetus is particularly vulnerable, estetrol is deemed to be a particularly safe biogenic estrogen. Side-effects are not expected to occur, particularly not if the serum levels resulting from the exogenous administration of such estrogens do not substantially exceed naturally occurring (fetal) concentrations. With synthetic estrogens such as ethinyl estradiol there is a (dose dependent) risk of undesirable side-effects, such as thromboembolism, fluid retention, nausea, bloating, cholelithiasis, headache, breast pain and an enhanced risk of breast cancer with longer term usage.

In a preferred embodiment of the present invention the estrogenic substance contains 4 hydroxyl groups. Also, in the aforementioned formula, $R_1$ preferably represents a hydrogen atom. In said formula preferably at least 2, more preferably at least 3 of the groups $R_1$, $R_2$, $R_3$ and $R_4$ represent a hydrogen atom.

The estrogenic substances according to the formula encompass various enantiomers since the carbon atoms that carry hydroxyl-substituents $R_5$, $R_6$ and $R_7$ are chirally active. In one preferred embodiment, the present estrogenic substance is 15α-hydroxy substituted. In another preferred embodiment the substance is 16α-hydroxy substituted. In yet another preferred embodiment, the substances is 17β-hydroxy substituted. Most preferably the estrogenic substances are 15α,16α,17β-trihydroxy substituted.

In another preferred embodiment of the present invention $R_3$ represents a hydroxyl group or an alkoxy group. In another preferred embodiment the groups $R_1$, $R_2$ and $R_4$ represent hydrogen atoms, in which case, if $R_3$, $R_5$, $R_6$ and $R_7$ are hydroxyl groups, the substance is 1,3,5 (10)-estratrien-3, 15,16,17-tetrol. A preferred isomer of the latter substance is 1,3,5 (10)-estratrien-3, 15α,16α,17β-tetrol (estetrol).

The invention also encompasses the use of precursors of the estrogenic substances that constitute the active component in the present method. These precursors are capable of liberating the aforementioned estrogenic substances when used in the present method, e.g. as a result of metabolic conversion. These precursors are preferably selected from the group of androgenic precursors as well as derivatives of the present estrogenic substances. Suitable examples of androgenic precursors include androgens that can be converted into the present estrogenic substances through in vivo aromatisation. Examples of derivatives of the present estrogenic substances that can suitably be used as precursors include such substances wherein the hydrogen atom of at least one of the hydroxyl groups has been substituted by an acyl radical of a hydrocarbon carboxylic, sulfonic acid or sulfamic acid of 1-25 carbon atoms; tetrahydrofuranyl; tetrahydropyranal; or a straight or branched chain glycosidic residue containing 1-20 glycosidic units per residue.

Typical examples of precursors which can suitably be used in accordance with the invention are esters that can be obtained by reacting the hydroxyl groups of the estrogenic substances with substances that contain one or more carboxy ($M^{+-}OOC$—) groups, wherein $M^+$ represents a hydrogen or (akali)metal cation. Hence, in a particularly preferred embodiment, the precursors are derivatives of the estrogenic substances, wherein the hydrogen atom of at least one of the hydroxyl groups in said formula has been substituted by —CO—R, wherein R is a hydrocarbon radical comprising from 1-25 carbon atoms. Preferably R is hydrogen, or an alkyl, alkenyl or aryl radical comprising from 1-20 carbon atoms.

The benefits of the present invention are most pronounced when the composition is used in longer term hormone replacement therapy so as to minimise the negative effects of chronic hypoestrogenism. Therefore, the method of hormone replacement therapy, preferably, comprises administering the estrogenic component for a period of at least 1 month, more preferably of at least 3 months. In a preferred embodiment of the present invention the estrogenic component is administered during a period of at least 4 months, preferably of at least 6 months. The estrogenic component is usually administered uninterruptedly during a period of at least 10 days, preferably of at least 20 days. The interruption intervals preferably do not exceed a period of 20 days, more preferably they do not exceed a period of 10 days. In a particularly preferred embodiment of the invention, the estrogenic component is administered uninterruptedly during a period of at least 4, preferably at least 6 months.

The term "uninterrupted" as used here, means that the estrogenic component is administered at relatively regular intervals, with no (therapeutically) significant interruptions. Naturally, minor interruptions may occur that do not affect the overall effectiveness of the present method, and indeed such aberrations are encompassed by the present invention. In a preferred embodiment, and more arithmetically, the administration regimen is deemed to be uninterrupted if the longest interval between 2 subsequent administrations is not more than 3.5 times as long as the average interval. Even more preferably said longest interval is not more than 2.5 times, most preferably not more than 1.5 times as long as the average interval.

The present method may suitably employ enteral or parenteral administration of the estrogenic component. The term "parenteral administration" as used in here encompasses transdermal, intranasal, intravaginal, pulmonary, buccal, subcutaneous, intramuscular and intrauterine administration. The term "enteral administration" includes oral as well as rectal administration.

Preferably the mode of administration is selected from the group consisting of oral, transdermal, intranasal, intravaginal, pulmonary, rectal, buccal, subcutaneous, intramuscular or intrauterine administration. More preferably the mode of administration is selected from the group consisting of oral, transdermal, subcutaneous, intramuscular, intranasal, pulmonary and vaginal administration. In a particularly preferred embodiment the present method employs oral, transdermal, intranasal, intravaginal or rectal administration. Even more preferably the present method employs oral or transdermal administration.

Oral, intranasal, rectal, buccal and pulmonary administration are ideally suited for (at least) once daily administration. Transdermal administration is advantageously applied at frequencies between once a day and once a month. Intravaginal and intrauterine administrations are advantageously operated at administration frequencies between once weekly and once monthly. Subcutaneous and intramuscular administration are suitably done in the form of depot injections at intervals of 1 week to 6 months, preferably at intervals of 4 weeks to 3 months.

For reasons of convenience and also to achieve high compliance rates, the present method preferably utilises administration intervals of 1 day, 1 week or 1 month. Regimens that employ once daily oral or intranasal administration, once weekly transdermal or once monthly intravaginal or subcutaneous administration are particularly preferred.

Irrespective of the mode of administration, the estrogenic component is preferably administered in an amount effective to achieve a blood serum concentration of at least 1 nanogram per litre, more preferably of at least 10 nanogram per litre, most preferably at least 100 nanogram per litre. Generally the resulting blood serum concentration of the estrogenic component will not exceed 100 µg per litre, preferably it will not exceed 50 µg per litre, more preferably it will not exceed 25 µg per litre.

In accordance with the present method the estrogenic component is usually administered in an amount of less than 1 mg per kg of bodyweight per day, preferably of less than 0.4 mg per kg of bodyweight per day. In order to achieve a significant impact from the administration of the estrogenic component, it is advisable to administer in an amount of at least 1 µg per kg of bodyweight per day. Preferably, the administered amount is at least 5 µg per kg of bodyweight per day.

Oral administration of the active component is preferably done in an amount of less than 400 µg per kg of bodyweight per day, preferably of less than 200 µg per kg of bodyweight per day. In order to achieve a significant impact from the administration of the active component, it is advisable to orally administer in an amount of at least 2 µg per kg of bodyweight per day. Preferably, the orally administered amount is at least 5 µg per kg of bodyweight per day. In the present method, particularly when used in humans, the estrogenic component is usually administered in an average dosage of at least 0.05 mg per day, preferably of at least 0.1 mg per day. The average maximum parenteral or rectal dosage is normally kept below 40 mg per day, preferably below 20 mg per day.

The present method of hormone replacement therapy comprises administering to a person in need of such a therapy an effective amount of the estrogenic component. The amounts needed to be effective will differ from individual to individual and are determined by factors such as the individual's level of estrogen deficiency, body weight, route of administration and the efficacy of the particular estrogenic substance used. Suitably, the method according to the invention will comprise the daily administration of at least 0.001, preferably of 0.001-1000 mg of the estrogenic component. Preferably the HRT-method of the invention comprises orally or transdermally administering, on a daily basis, 0.01-1000 mg, and more preferably 0.1-100 mg of the estrogenic component.

The inventors have surprisingly found that the present estrogenic substances display a much higher affinity to the estrogen receptor α (ERα) than to the estrogen receptor β (ERβ). This characteristic is an unique feature of these estrogenic substances which is believed to be intrinsically linked to the beneficial properties of these substances as manifested in the present method.

Given the complexity of ER signalling, along with the tissue-specific expression of ERα and ERβ and its co-factors, it is now recognised that ER ligands can act as estrogen agonists or even as estrogen antagonists in a tissue-specific manner. In case of the present estrogenic substances, the interaction with co-factors may result in very different biological actions of these substances, in different tissues.

It is known that the ERα and ERβ receptors, have significantly different amino acid sequences in the ligand binding domain and carboxy-terminal transactivation domains (about 56% amino acid identity), and only 20% homology in their amino-terminal transactivation domain. This explains why the present estrogenic substances can exhibit a much higher affinity to the ERα than the ERβ receptor.

The present estrogenic substances, although displaying a much higher affinity for ERα than ERβ, are not to be regarded as antagonists of the ERβ receptor. In order to rule out the risk of undesirable proliferative effects, it is advisable to not employ unduly high doses of the present estrogenic substances. Preferably the estrogenic component is administered in an average daily dose that does not exceed 50 mg, 40 mg, 30 mg or 20 mg. More preferably the average daily dose does not exceed 10 mg. Most preferably the average daily dose does not exceed 5 mg.

In a particularly preferred embodiment of the invention the method employs oral administration of the active estrogenic component. The term oral administration as used in here also encompasses oral gavage administration. The inventors have surprisingly found that, despite its low potency, estetrol and related estrogenic substances may advantageously be administered orally. Although the inventors do not wish to be bound by theory, it is believed that the unexpected efficacy of orally administered estetrol-like substances results from the combination of special pharmacokinetic and pharmacodynamic properties of these substances.

The inventors have discovered that the oral bioavailability of estetrol-like substances is surprisingly high and that their in vivo half-life is considerably longer than that of biogenic estrogens. Thus, even though estetrol and estetrol-like substances have relatively low estrogenic potency, they may effectively be administered orally because the oral dosages required to achieve the desired effect are similar to those already used for e.g. 17β-estradiol.

Another important advantage of oral administration of estetrol and estetrol-like substances resides in the fact that the hepatic effects of these substances are deemed to be minimal since they are hardly metabolised during the so called "first pass". The first-pass effect of drugs given orally refers to the process of drug degradation by the liver during a drug's transition from initial ingestion to circulation in the blood stream. After resorption from the intestinal lumen, orally applied active ingredients enter the organism via the liver. This fact is of specific importance for estrogenic agents as the liver is a target organ for estrogens; oral intake of estrogens results in strong estrogenic effects in the liver. Therapeutically equivalent doses of biogenic estrogens, when applied orally, result in clear responses of hepatic parameters, such as increase of SHBG, CBG, angiotensinogen and HDL (high density lipoprotein). These hepatic effects of estrogens are also observed when equine estrogen formulations (so-called conjugated estrogens) are used. Ethinyl estradiol and diethylstilbestrol (DES) have an even greater hepatic estrogenicity. Elger et al., J. Steroid Biochem. Molec. Biol. (1995), 55(3/4), 395-403, have reported that EE or DES have much higher hepato-cellular than systemic estrogenicity: in relation to FSH-secretion inhibitory activity these estrogens are 4-18 times more active in the liver than estrone sulfate.

In a particularly preferred embodiment of the invention the pharmaceutical composition according to invention is designed for daily administration, i.e. it represents a daily dosage unit. In accordance with this preferred embodiment the daily dosage unit contains from 0.001-1000 mg of the estrogenic component. More preferably the amount of estrogenic component is within the range of 0.01-1000 mg. Even more preferably said amount is in the range of 0.1-100 mg. Especially preferred are daily dosage units that contain at most 50 mg, 40 mg, 30 mg, 20 mg or 10 mg of the estrogenic component. Most preferably the daily dosage unit contains at most 5 mg of the estrogenic component.

As mentioned before, it is an important advantage of the present pharmaceutical composition that it can be used to deliver the benefits of estrogen replacement therapy without the drawback of significant estrogen induced endometrial proliferation, thereby obviating the need for using supplementary hormones, e.g. progestogens and anti-progestogens, to suppress such endometrial proliferation.

Hence, in accordance with the present invention, the composition contains virtually no progestogens or anti-progestogens. More preferably the present composition contains no progestogens or anti-progestogens. The combined use of estrogens and gonadotropin-releasing hormone, estrogens and luteinizing hormone releasing hormone and estrogens and antisense oligonucleotides to the follicle stimulating hormone receptor gene has been suggested in the prior art documents which were discussed above. In a preferred embodiment, the present method does not employ a gonadotropin-releasing hormone analogue. In another, preferred embodiment, the present method does not employ a luteinizig hormone releasing hormone. In yet another preferred embodiment, the method does not employ an antisense oligonucleotide that is complementary to the nucleotide sequence of the follicle stimulating hormone (FSH) receptor.

Since the benefits of the present invention can be obtained by using the present substances and their precursors as the sole active ingredients, it is preferred that the composition contains virtually no other sex hormones or sex hormone antagonists other than the estrogenic component. More preferably, the total level of sex hormones or sex hormone antagonists other than the estrogenic component is less than 1%, and most preferably it is less than 0.1% by weight of the estrogenic component.

However, it should be understood that the present composition may suitably comprise a variety of other supplementary pharmaceutical components. In particular, it can be advantageous to additionally include androgens or anti-resorptive agents such as calcitonins and bisphosphonates. Also, it may be beneficial to incorporate components that act as anabolic agents, such as fluoride salts, growth hormone, insulin-like growth factors, parathyroid hormone, statins, calcium and vitamin D. Furthermore, it may advantageous to include cardiovascular protective agents, such as statins and folic acid.

Another aspect of the invention is concerned with a drug delivery system for enteral or parenteral administration, said drug delivery system being selected from the group consisting of oral dosage units, systems for intravaginal or rectal delivery, injectable or implantable depot preparations, inhalers, nasal sprays and transdermal delivery systems, wherein the system contains at least 1 µg of the present estrogenic component and virtually no progestogen or anti-progestogen. Preferably the drug delivery system does not contain any progestogen or anti-progestogen at all.

The present drug delivery systems preferably contain at least 2 µg of the estrogenic component, more preferably at least 5 µg of said estrogenic component. More preferably the amount of the estrogenic component within the drug delivery system is at least 10 µg, most preferably it will be at least 30 µg. The amount of the estrogenic component within the formulation will normally not exceed 500 mg. Preferably the amount will not exceed 300 mg, most preferably it will not exceed 200 mg.

The oral dosage unit according to the invention is preferably a solid or semi-solid dosage form such as tablets, capsules, cachets, pellets, pills, powders and granules. The term "solid or semi-solid dosage form" also encompasses capsules that contain a liquid, e.g. an oil, in which the present estrogenic component is dissolved or dispersed. Tablets and equivalent solid and semi-solid dosage forms can suitably contain materials such as binders (e.g. hydroxypropylmethyl cellulose, polyvinyl pyrrolidine, other cellulosic materials and starch), diluents (e.g. lactose and other sugars, starch, dicalcium phosphate and cellulosic materials), disintegrating agents (e.g. starch polymers and cellulosic materials) and lubricating agents (e.g., stearates and talc).

Transdermal delivery systems include patches, gels, tapes and creams, and can contain excipients such as solubilisers, permeation enhancers (e.g. fatty acids, fatty acid esters, fatty alcohols and amino acids), hydrophilic polymers (e.g. polycarbophil and polyvinyl pyrrolidine) and adhesives and tackifiers (e.g. polyisobutylenes, silicone-based adhesives, acrylates and polybutene).

Transmucosal (notably rectal and intravaginal) delivery systems include patches, tablets, suppositories, pessaries, gels, and creams, and can contain excipients such as solubilizers and enhancers (e.g. propylene glycol, bile salts and amino acids), and other vehicles (e.g. polyethylene glycol, fatty acid esters and derivatives, and hydrophilic polymers such as hydroxypropylmethyl cellulose and hyaluronic acid).

Injectable or implantable depot preparations include injectable fluids and implantation tablets. Suitable fluid carrier components are physiologically compatible diluents wherein the active agents can be dissolved, suspended. An example of a diluent is water, with or without addition of electrolyte salts or thickeners. Thus, the depot formulation can be, for example, an aqueous microcrystalline' suspension. Oils are particularly suitable as diluents, with or without the addition of a solubiliser, of a surfactant, or of a suspension or emulsifying agent. Examples of suitable oils include arachidis oil, olive oil, peanut oil, cottonseed oil, soybean oil, castor oil, and sesame oil. Examples of solubilisers include benzyl alcohol and benzyl benzoate. Depot preparations offer the advantage that a single injection or implantation suffices for one or several months. Duration of the depot effect depends the nature of the estrogenic component (the ester precursors being preferred as they display a slower release), the amount of the estrogenic component as well as on the type of carrier substance that releases the active agent. Generally, the duration will be in the range, of 10-30 days, but longer or shorter times can also be achieved.

Other delivery systems that can be used for administering the pharmaceutical composition of the invention include intranasal and pulmonary delivery systems such as sprays and microparticles.

Yet another embodiment of the present invention is concerned with a kit containing at least 20 oral dosage units that contain the present estrogenic component. The present kit may suitably contain a combination of oral dosage units that contain the estrogenic component and placebo's. Preferably, however, each dosage unit within said kit comprises the present estrogenic component. In addition, each dosage unit advantageously comprises an amount of estrogenic component that is sufficient for 10-48 hours, meaning that the units are to be administered in the present hormone replacement method at intervals between 10 and 48 hours. The dosage units are preferably tablets or capsules. Here the term tablet is meant to encompass other forms of solid bodies that can suitably be used for oral administration, such as pills, pellets and others.

The present invention is further illustrated by the following examples, which, however, are not to be construed as limiting. The features disclosed in the foregoing description, in the following examples and in the claims may, both separately and in any combination thereof, be material for realising the invention in diverse forms thereof.

EXAMPLES

Example 1

Vaginal cornification was chosen as a tissue-specific and estrogen-sensitive endpoint to determine the estrogenicity of estetrol (E4), after both oral and subcutaneous administration, in hypoestrogenic rats. 17α-ethinylestradiol (EE), 17β-estradiol (E2) and vehicle (10% ethanol/sesame oil) served as controls in these bioassays.

Uterine weight increase in the rat is more commonly used as a measure of estrogenicity. However, uterine weight also responds, to progesterone, testosterone, and other agents not characteristically regarded as estrogens. In the early 1920s it was discovered that follicular fluid from the pig ovary contained a factor(s) that caused cornification/keratinization of the vaginal epithelium in the rat (Allen and Doisy, 1923, JAMA, 81, 819-821; Allen and Doisy, 1924, Am. J. Physiol., 69, 577-588). The so-called vaginal cornification response in rats subsequently provided a bioassay for testing estrogenicity. Vaginal epithelial cornification/keratinization in ovariectomized rats can be produced only by compounds considered to be true estrogens (Jones et al, 1973, Fert. Steril. 24, 284-291). Vaginal epithelial cornification/keratinization represents, therefore, a highly selective endpoint to determine the potency of estrogens (Reel et al., 1996, Fund. Appli. Toxicol. 34, 288-305).

Adult intact female CD rats were ovariectomized to induce estrogen deficiency. Vaginal lavages were performed daily for seven days to ensure that the rats demonstrated castrate vaginal smears (predominance of leukocytes in the vaginal smear, and similar in appearance to a diestrous vaginal smear). Castrate vaginal smears are indicative that complete ovariectomy was achieved. Treatment commenced following completion of the 7 days of smearing (day 0=first day of dosing). Animals were dosed, once daily for 7 consecutive days. Daily vaginal lavages continued to be obtained for 7 days after dosing was initiated in order to detect vaginal cornification, as an indication of an estrogenic response. A drop of vaginal washings was placed on a glass slide and examined by light microscopy to detect the presence or absence of cornified epithelial cells. Vaginal lavages were obtained prior to dosing on days 0-6 and prior to necropsy on day 7.

The vaginal cornification bioassay was performed in order to determine the estrogenic profile of E4 when given subcutaneously (sc) to ovariectomized adult rats. E2 was used as a positive control. The vehicle (10% ethanol/sesame oil) served as the negative control. Steroids were dissolved in absolute ethanol and then brought to the fmal concentration with sesame oil (10% ethanol in sesame oil). A vaginal estrogenic response occurred in 8/8 rats by day 2 and persisted through day 7 in rats injected sc with 50 µg/kg/day E2 for 7 days (Table 1). Animals treated with the vehicle did not exhibit vaginal epithelial cornification (Table 1). The onset of vaginal epithelial cornification was dose-dependent in rats injected sc with 0.1, 0.3, 1.0, and 3.0 mg/kg/day E4 and started at the same day of treatment (Day 2) as observed for E2 (Table 1). At 0.1 mg/kg/day E4 already 4/8 rats and at 0.3 mg/kg/day E4 even 7/8 rats exhibited a vaginal estrogenic response by day 7. At 1.0 and 3.0 mg/kg/day E4 all rats showed a vaginal estrogenic response by day 7 (Table 1).

TABLE 1

Vaginal estrogenic response in ovariectomized rats treated subcutaneously (sc) with 17β-estradiol (E2) or estetrol (E4). Data are expressed as the number of rats showing vaginal cornification over the number of rats (ratio) treated.

| Treatment Group | Dosing route | Number of Rats Exhibiting Estrogenic Response/ Number of Rats Treated Day of Study | | | | | | | |
|---|---|---|---|---|---|---|---|---|---|
| | | Day 0 | Day 1 | Day 2 | Day 3 | Day 4 | Day 5 | Day 6 | Day 7 |
| 0.05 mg/kg/day E2 | sc | 0/8 | 0/8 | 8/8 | 8/8 | 8/8 | 8/8 | 8/8 | 8/8 |
| Vehicle Control | sc | 0/8 | 0/8 | 0/8 | 0/8 | 0/8 | 0/8 | 0/8 | 0/8 |
| 0.1 mg/kg/day E4 | sc | 0/8 | 0/8 | 0/8 | 1/8 | 1/8 | 4/8 | 3/8 | 4/8 |
| 0.3 mg/kg/day E4 | sc | 0/8 | 0/8 | 1/8 | 5/8 | 7/8 | 6/8 | 7/8 | 7/8 |
| 1.0 mg/kg/day E4 | sc | 0/8 | 0/8 | 1/8 | 6/8 | 8/8 | 7/8 | 8/8 | 8/8 |
| 3.0 mg/kg/day E4 | sc | 0/8 | 0/8 | 3/8 | 8/8 | 8/8 | 8/8 | 8/8 | 8/8 |

The vaginal cornification bioassay was performed in order to determine the estrogenic profile of E4 when given orally (po) to ovariectomized adult rats. EE was used as a positive control. The vehicle (10% ethanol/sesame oil) served as the negative control. Steroids were dissolved in absolute ethanol and then brought to the final concentration with sesame oil (10% ethanol in sesame oil). A vaginal estrogenic response occurred in all rats (8/8) given 50 µg/kg/day EE po by day 7 (Table 2). Similarly, vaginal epithelial cornification was observed in all rats (8/8) treated po with either 0.1, 0.3, 1.0, or 3.0 mg/kg/day E4 by day 7 (Table 2), whereas animals treated with the vehicle did not exhibit vaginal epithelial cornification (0/8). Surprisingly, even in rats given relatively low doses of E4 (e.g. 0.1 mg/kg/day), the onset of vaginal cornification (defined as the amount of animals responding at days 1-3 of the study) was faster in po-treated than in sc-treated animals, demonstrating estetrol's superb bioavailability characteristics after oral administration exteriorized and removed and the musculature was closed with a single suture. The skin incision was closed using surgical staples.

Ten animals per treatment group were orally dosed once per day for four consecutive weeks. The dosing commenced 1 day after surgical removal of the ovaries and was administered by oral gavage using a syringe and stainless steel gavage needle at doses of 0.1 mg/kg /day EE, or either 2.5, 0.5 or 0.1 mg/kg/day E4. Vehicle control was daily administered to one group of OVX-animals and sham-operated rats. After treatment, anesthetized rats were subjected to cardiac puncture and asphyxiated by $CO_2$ inhalation. Tibiae and femura were removed, cleaned of soft-tissue and fixed and stored in 70% ethanol/saline at 4° C. (tibia) or saline at 4° C. (femura) until fuirther analysis.

Ex vivo peripheral Quantitative Computed Tomography (pQCT) was performed on the excised left tibiae using a Stratec XCT-RM and associated software (Stratec Medizin-

TABLE 2

Vaginal estrogenic response in ovariectomized rats treated orally (po) with 17α-ethinyl estradiol (EE) or estetrol (E4). Data are expressed as the number of rats showing vaginal cornification over the number of rats (ratio) treated.

| Treatment Group | Dosing route | Number of Rats Exhibiting Estrogenic Response/ Number of Rats Treated Day of Study | | | | | | | |
|---|---|---|---|---|---|---|---|---|---|
| | | Day 0 | Day 1 | Day 2 | Day 3 | Day 4 | Day 5 | Day 6 | Day 7 |
| 0.05 mg/kg/day EE | po | 0/8 | 1/8 | 3/8 | 8/8 | 8/8 | 8/8 | 8/8 | 8/8 |
| Vehicle Control (2 ml/kg/day) | po | 0/8 | 0/8 | 0/8 | 0/8 | 0/8 | 0/8 | 0/8 | 0/8 |
| 0.1 mg/kg/day E4 | po | 0/8 | 0/8 | 1/8 | 7/8 | 8/8 | 8/8 | 8/8 | 8/8 |
| 0.3 mg/kg/day E4 | po | 0/8 | 0/8 | 1/8 | 7/8 | 8/8 | 8/8 | 8/8 | 8/8 |
| 1.0 mg/kg/day E4 | po | 0/8 | 0/8 | 4/8 | 8/8 | 8/8 | 8/8 | 8/8 | 8/8 |
| 3.0 mg/kg/day E4 | po | 0/8 | 0/8 | 6/8 | 8/8 | 8/8 | 8/8 | 8/8 | 8/8 |

Example 2

The ovariectomized aged rat was used as a model for the human disease osteoporosis. This is an established animal model, recommended by the United States Food and Drug Administration (FDA), to evaluate and assess potential agents for osteoporosis prevention and therapy. The anti-resorptive efficacy of estetrol (E4) was tested by ex vivo measuring total and trabecular bone mineral density and bone strength after 4 weeks of treatment at necropsy. 17α-ethinyl-estradiol (EE) and vehicle (1% ethanol/arachidis oil) served as controls in this bioassay.

Three months old female Sprague-Dawley rats were either sham-operated (Sham) or ovariectomized (OVX) one day prior to commencement of the dosing study. Animals were anesthetized using a ketamine/xylazine anesthetic mixture and underwent a bilateral ovariectomy or were sham-treated. A section of hair on the dorsal surface was shaved and an incision made overlying the lumbar region of the spine. The skin was separated from the underlying fascia so that a second incision could be made through the abdominal musculature approximately caudal to the kidneys. The ovaries were then technik GmbH, Pforzheim; Germany, software version 5.40). The scans were performed at 12% of the total length from the proximal end of the tibiae. The positions were verified using scout views and one 0.5-mm slice perpendicular to the long axis of the tibial shaft was acquired from each site. The scans were analyzed using a threshold for delineation of the external boundary. The total and trabecular bone mineral content, area and density at each site were determined. Mean values are shown in Table 3. Furthermore, pQCT data for mean total bone mineral density are depicted in FIG. 1.

Comparison of the pQCT densitometry data from the proximal tibiae of Sham-operated and OVX-rats demonstrated a consistent loss of total and trabecular bone in the OVX-group, as expected (Table 3, FIG. 1). Furthermore, there was a consistent dose-dependent increase for each of the parameters associated with total and trabecular bone mineral content and bone mineral density in. the animals orally treated with E4 (Table 3, FIG. 1). As compared to hypoestrogenic OVX-rats receiving vehicle treatment alone, 0.5 and 2.5 mg/kg/day E4 prevented bone resorption as exemplified by total bone mineral density levels equivalent to sham-operated rats (FIG. 1). Furthermore, the anti-resorptive activity achieved with the highest dose of E4 (235 mg/kg/day) was equivalent to the effect seen with the positive control EE.

TABLE 3 pQCT densitometry data from the proximal tibiae of Sham- and OVX-rats orally (po) reated with 17α-ethinyl estradiol (EE), estetrol (E4) or vehicle. Data are expressed as the mean values obtained for each group (n = 10).

| Treatment Group (n = 10) | Dosing route | Mean Total Bone Mineral | | | Mean Trabecular Bone Mineral | | |
|---|---|---|---|---|---|---|---|
| | | Content (mg/mm) | Area (mm$^2$) | Density (mg/cm$^3$) | Content (mg/mm) | Area (mm$^2$) | Density (mg/cm$^3$) |
| SHAM + Vehicle | po | 9.36 | 14.10 | 664.07 | 1.49 | 6.34 | 235.48 |
| OVX + Vehicle | po | 8.76 | 14.47 | 606.61 | 1.10 | 6.51 | 169.63 |
| OVX + 0.1 mg/kg/day EE | po | 9.66 | 13.87 | 697.48 | 1.81 | 6.24 | 290.16 |
| OVX + 0.1 mg/kg/day E4 | po | 8.46 | 14.41 | 588.62 | 0.96 | 6.48 | 145.46 |
| OVX + 0.5 mg/kg/day E4 | po | 9.74 | 14.80 | 660.57 | 1.60 | 6.65 | 243.31 |
| OVX + 2.5 mg/kg/day E4 | po | 9.61 | 13.59 | 707.11 | 1.89 | 6.12 | 309.58 |

Ex vivo evaluation of bone biomechanical strength was performed with an indentation test at the distal femura. Prior to mechanical testing femura were rinsed in cold saline and carefully cleaned of any remaining adherent soft tissue. A 3-mm segment of the distal femoral metaphysis was cut directly proximal to the femoral condyle with a low-speed diamond saw under constant saline irrigation. The load was applied with a cylindrical indenter (with a flat testing face of 1.6 mm diameter) to the center of marrow cavity on the distal face of the segment. The indenter was allowed to penetrate the cavity at a constant displacement of 6 mm/min to a depth of 2 mm before load reversal.

TABLE 4

Indentation testing of the distal femur of Sham- and OVX-rats orally (po) treated with 17α- ethinyl estradiol (EE), estetrol (E4) or vehicle. Data are expressed as the mean values obtained for each group (n = 10).

| Treatment Group (n = 10) | Dosing route | Maximum load (N) | Stiffness (N/mm) | Energy (mJ) | Ultimate strength (N/mm2) |
|---|---|---|---|---|---|
| SHAM + Vehicle | po | 8.61 | 131.96 | 0.48 | 4.57 |
| OVX + Vehicle | po | 2.77 | 42.08 | 0.21 | 1.47 |
| OVX + 0.1 mg/kg/day EE | po | 9.05 | 169.12 | 0.53 | 4.80 |
| OVX + 0.1 mg/kg/day E4 | po | 1.50 | 28.00 | 0.09 | 0.80 |
| OVX + 0.5 mg/kg/day E4 | po | 7.25 | 132.57 | 0.31 | 3.85 |
| OVX + 2.5 mg/kg/day E4 | po | 13.07 | 173.12 | 0.68 | 6.94 |

Figure 2:
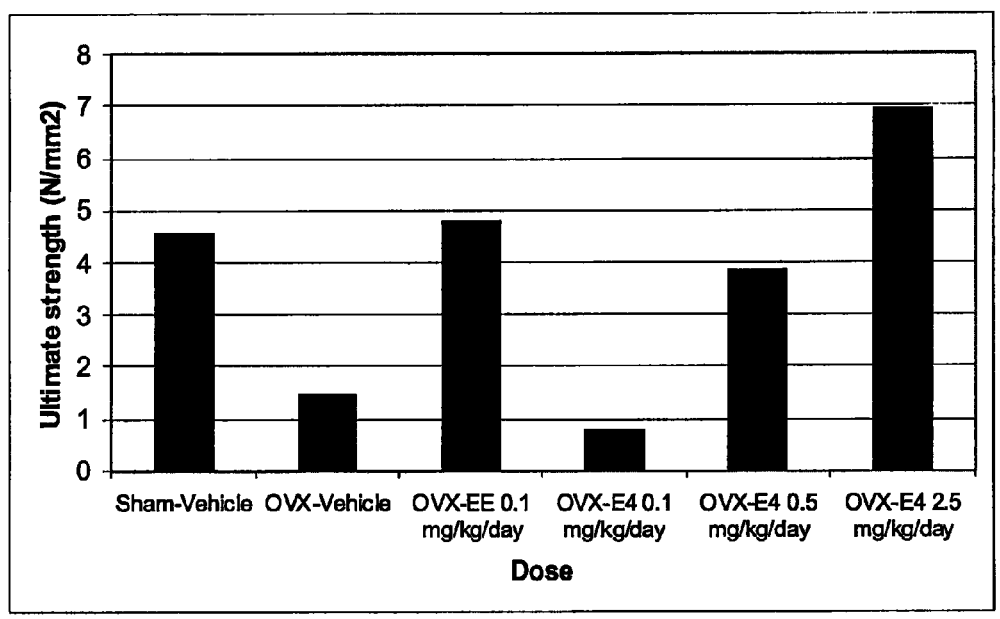
FIG. 2 is a graph showing the mean ultimate strength of the distal femur of Sham- and OVX-rats orally (po) treated with 17α-ethinyl estradiol (EE), estetrol (E4) or vehicle for 4 consecutive weeks. Data are expressed as the mean values obtained for each group (n=10).

The maximum load, stiffness and energy absorbed were determined from load displacement curves. Ultimate strength was calculated by dividing the maximum load by the indenter area. Mean values of maximum load, stiffness, energy and ultimate strength are shown in Table 4. Furthermore, mean ultimate strength values are depicted in FIG. 2. As compared to Sham-operated rats, the mechanical strength of cancellous bone appeared to be markedly reduced in OVX-rats treated with vehicle alone (Table 4, FIG. 2). Reductions in maximum load, stiffness, energy and ultimate strength were −68%, −68%, −27% and −68%, respectively, clearly accompanying the bone mineral density loss in estrogen deficient rats. Oral treatment of hypoestrogenic OVX-rats with E4 prevented the declines in maximum load, stiffness, energy and ultimate strength, in a dose-dependent manner(Table 4, FIG. 2). In addition, the efficacy achieved with the highest dosis of E4 (2.5 mg/kg/day) even appears superior to that of the positive control EE (Table 4, FIG. 2).

Example 3

The morphine-dependent ovariectomized (OVX) rat was used as a model for postmenopausal hot flush. The potency of estetrol (E4) to prevent tail skin temperature rises, normally accompanied by a drop in core body temperature, after naloxone-induced opiate withdrawel was tested. 17α-ethinyl-estradiol (EE) and vehicle. (hydroxy propyl-beta-cyclodextrin 20% wt/vol) served as controls in this bioassay.

The most common and characteristic symptom of human menopause is the hot flush, which is experienced by over 70% of menopausal females. Whiule the exact mechanism underlying this vasomotor instability is unknown, the characteristic features of the hot flush appear to reflect a centrally mediated adaptation to a progressive decline in the levels of estrogens. In women experiencing the hot flush the symptoms are manifested by 1) rapid; regional elevations in skin temperature; 2) a decrease in core body temperature; 3) an increased heart rate with no change in blood pressure; and 4) closely timed surges in release of luteinizing hormone (LH) and β-endorphin.

The morphine-dependent ovariectomized (OVX) rat model has been proposed by several investigators (Katovich et al, 1986, Maturitas, 67-76; Merchenthaler et al. 1998, Maturitas, 307-316) as an animal model for the hot flush. During opiate withdrawal with the morphine antagonist naloxone, tail skin temperature (TST) rises and this rise is accompanied by a drop in core body temperature. In addition, the temperature changes are accompanied by surges in LH and a transient tachycardia. These events are similar in magnitude and temporal nature to those observed in the menopausal hot flush.

8-week-old OVX rats were treated orally (po) with estetrol (E4), 17α-ethinyl estradiol (EE) or vehicle control (hydroxy propyl-beta-cyclodextrin 20% wt/vol) for seven consecutive days prior to, and on the morning of naloxone-induced opiate withdrawal in morphine-dependent animals. Three days prior to the commencement of dosing, animals were anesthetized using a ketamine/xylazine anesthetic mixture and underwent a bilateral ovariectomy. A section of hair on the dorsal surface was shaved and an incision made overlying the lumbar region of the spine. The skin was separated from the underlying fascia so that a second incision could be made through the abdominal musculature approximately caudal to the kidneys. The ovaries were then exteriorized and removed and the musculature was closed with a single suture. The skin incision was closed using surgical staples. Six rats per treatment group were dosed once per day for eight consecutive days prior to and including the day of naloxone-induced opiate withdrawal (the hot flush session). The dosing commenced three days after surgical removal of the ovaries and was administered by oral gavage using a syringe and stainless steel gavage needle. Morphine dependency was induced by implantation of subcutaneous pellets containing 75-mg morphine. The first pellet was implanted five days before the hot flush session under a light inhalation anesthesia. Three days before the hot flush session, two additional morphine pellets were implanted under the same conditions.

For the hot flush manipulations the animals were placed in a test cage. Following a 5-10 minute adaptation period, the rats were aniesthetized with ketamine HCl approximately 10 minutes prior to the hot flush session. A temperature sensitive electrode was fixed to the ventral surface of the tail with tape and the electrode was connected to a multi-channel temperature recorder. The tail-skin temperature was recorded until it was stable and the animals were then injected with naloxone HCl (1 mg/kg). The temperature recordings then continued for a period of 60 minutes and the temperature was reported at 5-minute intervals. At the completion of the hot flush session, all animals were killed using $CO_2$ asphyxiation followed by cervical dislocation.

Figure 3:
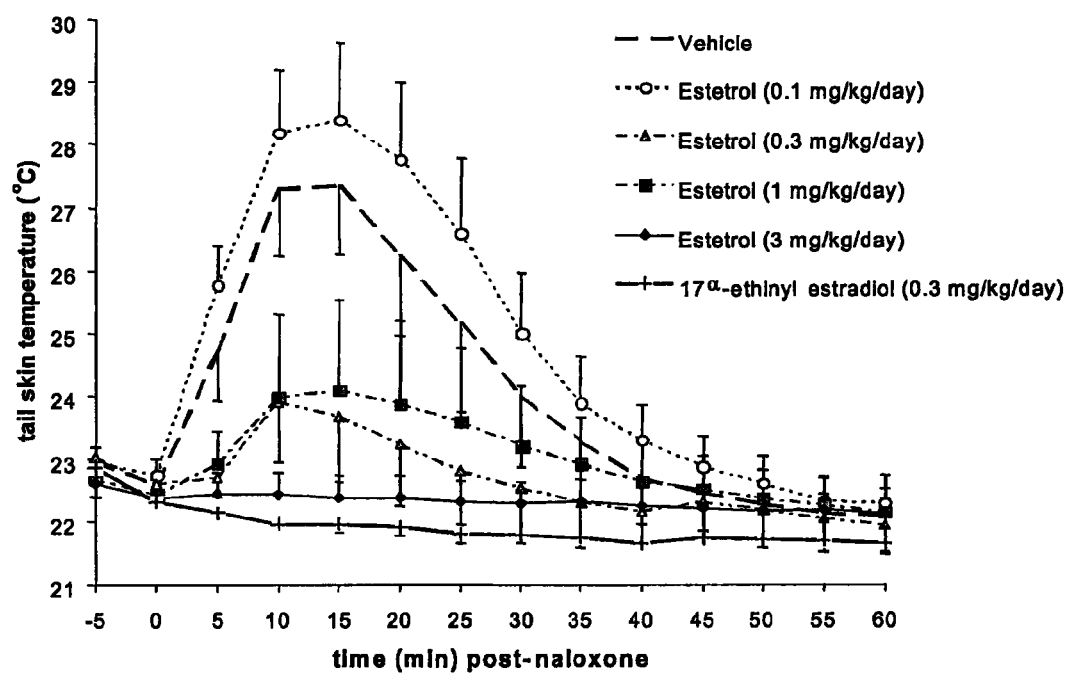
FIG. 3 is a graph showing the effects of estetrol (E4) and 17α-ethinyl estradiol (EE) on the naloxone induced hot flush response in female ovariectomized rats.

As expected, vehicle control was ineffective in preventing the naloxone-induced TST increases in the morphine addicted OVX rats (FIG. 34). 17α-ethinyl estradiol (EE), at the single dose tested of 0.3 mg/kg/day; prevented the naloxone-induced TST increases in the morphine addicted OVX rats (FIG. 3). Oral treatment with estetrol (E4) showed a clear dose-dependendent effect (FIG. 3). The three highest doses of E4 (0.3, 1.0 and 3.0 mg/kg/day) all attenuated the TST, with the highest dose (3.0 mg/kg/day) having a suppressive response similar to the potent oral estrogen, 17α-ethinyl estradiol (EE).

Example 4

Uterine weight increase in the rat was chosen as another relevant tissue-specific endpoint to determine the hormonal potency of estetrol (E4), particularly in relationship to its hormonal potency to induce vaginal cornification and to correct for vaginal atrophy. Orally (po) administered E4 was therefore tested in a modified 7-day vaginal cornification bioassay (see also example 1), including uterine wet weight measurements at necropsy, to account for vaginal and uterotrophic effects.

The uterotrophic response has been used for many years to assess estrogenic activity. The typical bioassay uses female rats with low levels of endogenous estrogens (e.g., ovariectomized adults or immature animals). In most assay designs the animals are dosed once or twice daily for 3 or 4 days, and twenty-four hours after the final dose the animals are killed, and the uteri excised and weighed. In the current bioassay, vaginal epithelial cornification, and uterine weight gain was evaluated in ovariectomized adult rats over a 7-day period. In this way, two distinct estrogen sensitive parameters could be evaluated concurrently.

Adult intact female CD rats were ovariectomized to induce estrogen deficiency. Vaginal lavages were performed daily for seven days to insure that the rats demonstrated castrate vaginal smears (predominance of leukocytes in the vaginal smear, and similar in appearance to a diestrous vaginal smear). Castrate vaginal smears are indicative that complete ovariectomy was achieved. Treatment commenced following completion of the 7 days of smearing to demonstrate complete ovariectomy (day 0=first day of dosing). Animals were orally dosed, once daily for 7 consecutive days with vehicle control (10% ethanol/sesame oil) or either 0.1, 0.3, 1.0, or 3.0 mg/kg/day E4. Daily vaginal lavages continued to be obtained for 7 days after dosing was initiated in order to detect vaginal cornification, as an indication of an estrogenic response. A drop of vaginal washings was placed on a glass slide and examined by light microscopy to detect the presence or absence of cornified epithelial cells. The cells present in the vaginal washings were recorded. Vaginal lavages were obtained prior to dosing on days 0-6 and prior to necropsy on day 7.

On Study Day 7, following vaginal lavage 24 hours after the final dose, all rats were euthanized by $CO_2$ asphyxiation. An abdominal incision was made and the uterus excised, blotted and weighed. The occurrence of vaginal cornification, indicative of an estrogenic response, is an "all or none" response. Therefore, data were expressed as the number of rats showing a vaginal estrogenic response (for one or more days) over the number of rats treated (ratio). A Z-test of proportions was used to compare the four test groups to the vehicle control group. Group means±SEM were also calculated for the uterine weights. These data were not normally distributed and did not demonstrate homogeneity of variances. Therefore, a Kruskal-Wallis non-parametric ANOVA on ranks was performed and significant differences across the four treatment groups and the vehicle control were determined using Dunn's method.

In rats given a range of po E4 doses, the onset of vaginal cornification was dose-dependent (see Table 2). At day 7, all po E4 doses tested were above the threshold for eliciting a vaginal estrogenic response in the ovariectomized adult rat and significantly ($P<0.05$) different from the vehicle control (Table 5). In contrast, however, only E4, at po doses of 1.0 and 3.0 mg/kg/day, were found to increase uterine weight significantly ($p<0.05$) as compared to the vehicle control group (Table 5). We therefore conclude that estetrol has a pharmacologically favourable profile. It shows agonistic activity at the vaginal epithelium at low and intermediate doses at which uterotrophic activity is not observed. This finding indicates that, especially at lower dosages, there is no need of adjunctive progestogen administration to prevent unwanted uterotrophic effects.

TABLE 5

Vaginal cornification and and uterotrophic responses in ovariectomized rats treated orally (po) estetrol (E4). Data are expressed as rats showing vaginal cornification (responders) or not (non-responders). Uterine weight data are expressed as the mean values and SEM obtained for each group (n = 8). Significant differences to vehicle control are indcated.

| Treatment Group (n = 10) | Dosing route | Vaginal Cornification | | | Uterine weight (mg) | | |
|---|---|---|---|---|---|---|---|
| | | responders | Non-responders | Significantly different from vehicle ($P < 0.05$) | Mean | SEM | Significantly different from vehicle ($P < 0.05$) |
| OVX + Vehicle | po | 0 | 8 | n.a. | 100.1 | 3.9 | n.a. |
| OVX + 0.1 mg/kg/day E4 | po | 8 | 0 | yes | 149.2 | 4.4 | no |
| OVX + 0.3 mg/kg/day E4 | po | 8 | 0 | yes | 181.2 | 9.6 | no |
| OVX + 1.0 mg/kg/day E4 | po | 8 | 0 | yes | 253.7 | 24.0 | yes |
| OVX + 3.0 mg/kg/day E4 | po | 8 | 0 | yes | 308.4 | 15.3 | yes | n.a.: not applicable

Example 5

Endometrial proliferation was chosen as another relevant tissue-specific endpoint to determine the hormonal potency of estetrol after chronic (4-week), oral treatment in ovariectomized rats. An established 4-week animal model, also recommended for evaluation of agents for osteoporosis prevention and therapy, was used. E4's potency to induce endometrial proliferation was tested for orally (po) admninistered doses 2.5 and 0.5 mg/kg/day E4, which showed antiresorptive efficacy in ex vivo analyses of total and trabecular bone mineral density and bone strength (see example 2). 17α-ethinyl-estradiol (EE) and vehicle (1% ethanol/arachidis oil) served as additional controls in this bioassay.

Three months old female Sprague-Dawley rats were either sham-operated (Sham) or ovariectomized (OVX) one day prior to commencement of the dosing study as described in Example 2. Ten animals per treatment group were orally dosed once per day for four consecutive weeks. The dosing commenced 1 day after surgical removal of the ovaries and was administered by oral gavage using a syringe and stainless steel gavage needle at doses of 0.1 mg/kg /day EE, or either 2.5 or 0.5 mg/kg/day E4. Vehicle control was daily administered to one group of OVX-animals and sham-operated rats. After treatment, anesthetized rats were subjected to cardiac puncture and asphyxiated by $CO_2$ inhalation. The uterine horns were isolated and weighed and then fixed in 4% formaldehyde at 4° C. After 14 days fixation, uteri were dehydrated and embedded in paraffin. Serial sections of uterine horns were cut and stained with either Hematoxylin/osin (H/E) or Ki67 proliferation marker according to the method of von Rango et al. (1998, Hum. Reprod., 13, 3177-3189). Proliferative indices were determined by scoring positively labeled cells on Ki67 immunostained sections. Typically, for each datapoint 1000 luminal epithelial cells were evaluated.

Figure 4:
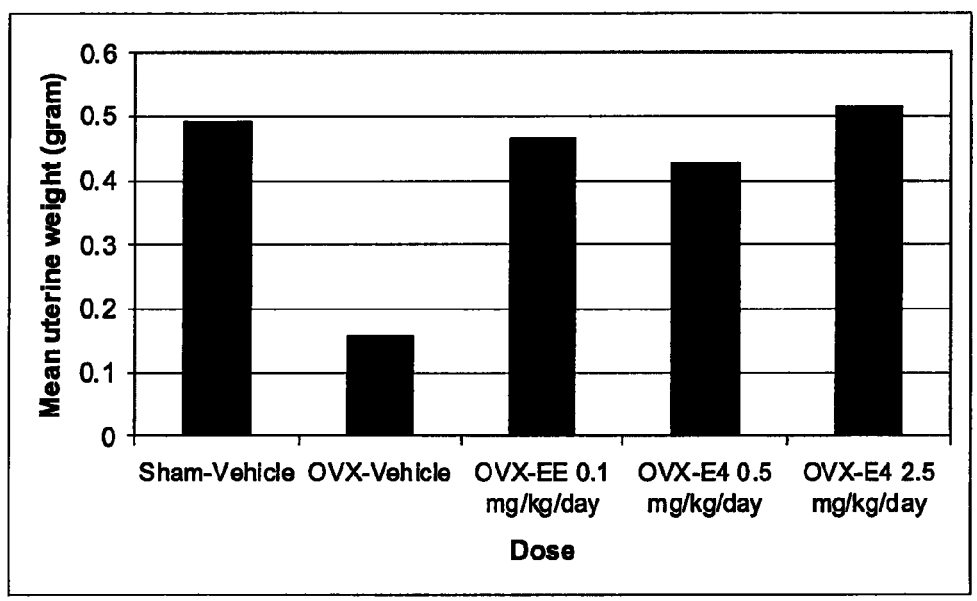
FIG. 4 is a graph showing the mean uterine weights of Sham- and OVX-rats orally (po) treated with 17a-ethinyl estradiol (EE), estetrol (E4) or vehicle for 4 consecutive weeks. Data are expressed as the mean values obtained for each group (n=10).
Figure 5:
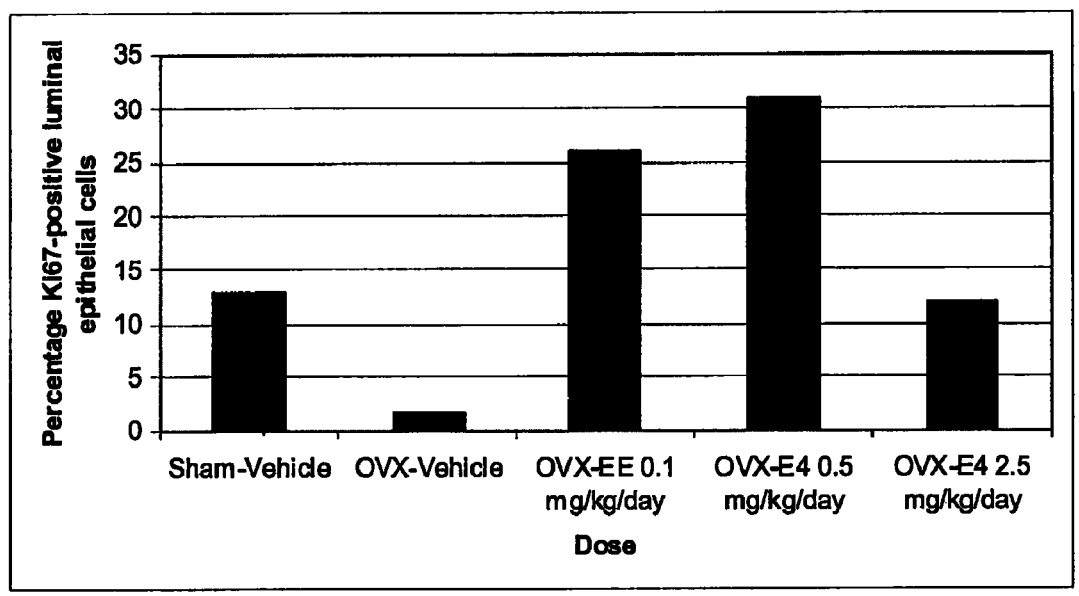
FIG. 5 is a graph showing the percentage Ki67-positive luminal epithelial cells in immunostained uterine sections of Sham- and OVX-rats orally (po) treated with 17α-ethinyl estradiol (EE), estetrol (E4) or vehicle for 4 consecutive weeks. Data are expressed as the mean percentages obtained for each group (n=10).

Mean uterine weight data are depicted in FIG. 4. Ovariectomy of rats resulted in uterine atrophy, as is evidenced by the loss of uterine weight in animals treated with vehicle alone compared to Sham-treated animals (FIG. 4). At oral dose levels, at which EE (0.1 mg/kg/day) and E4 (0.5 and 2.5 mg/kg/day) both prevent bone loss (see example 2), mean uterine weight were similar to Sham-vehicle treated animals (FIG. 4). Surprisingly, the percentage of Ki67-positive luminal epithelial cells declined with increasing doses of oral E4 treatment (FIG. 5). After 4-week oral treatment with 2.5 mg/kg/day E4 the percentage of Ki67-positive luminal epithelial cells was substantially less than in animals treated with 0.5 mg/kg/day E4 or even 0.1 mg/kg/day EE, suggesting less growth-promoting activity on endometrial tissue after chronic oral treatment with relatively high doses of E4 (FIG. 5). E4 therefore appears to have less estrogenic activity in the uterus than EE, especially at doses at which the effects of E4 on bone parameters (e.g. bone strength) are equipotent or better than of EE. It is therefore concluded that estetrol has a pharmacologically favourable profile. This finding indicates that there is no need of adjunctive progestogen administration to prevent unwanted endometrial proliferative effects.

Example 6

To evaluate the oral (po) and subcutaneous (se) bioavailability of estetrol (E4) and to determine the elimination half-life, single dose studies were performed in female Sprague Dawley rats followed by frequent blood sampling over a 24 hours interval.

Female Sprague Dawley rats were equipped with a permanent silatic heart catheter, as described by Kuipers et al. (1985, Gastroenterology, 88, 403-411). Rats were allowed to recover from surgery for 5 days and were than administered 0.05, 0.5, or 5 mg/kg E4 in 0.5 ml arachidis oil. For sc adninistration, E4 was injected in the neck area using a 1 ml syringe and 20 g needle. For po administration of E4, rats were lightly anaesthesized with halothene/$N_2O/O_2$ and E4 was directly applied intragastrically using a plastic stomach intubator. Blood samples were subsequently collected via the heart catheter in heparinized tubes at 0.5, 1, 2, 4, 8 and 24 hours. Erythrocytes were removed by centrifugation at 5000×g for 10minutes at 4° C. and blood plasma was stored at −20° C. After thawing the plasma samples, liquid-liquid extraction (hexane and diethyl ether) was employed to prepare the E4-containing plasma samples for HPLC analysis (Perkin Elmer 200) and tandem mass spectrometry using a PE Sciex 3000 tandem mass spectrometer and APCI interface. With each sample batch, a calibration curve with 6 calibrators was recorded. The calibration curve was calculated using linear regression (correlation coefficient>0.98), which permitted quantitation of plasma concentrations. For each rat plasma, sampled at different time intervals, data were collected.

Plasma E4 concentration data were analysed with "Win-NonLin, edition 3.1" and involved pharmacokinetic parameters for $C_{max}$, half-life and $AUC_{0-24}$. Especially, using the lower and intermediate dose levels of 0.05, 0.5 mg/kg, E4 demonstrated an oral bioavailability equal to the bioavailability obtained with sc administration (80-100%). At the highest dose level tested, 5.0 mg/kg E4, absorption kinetics gave rise to an oral bioavailability approximating 30-60% of sc administered E4. Interestingly, E4 demonstrated a relatively long half-life of 2-3 hours, enabling the detection of bioactive levels of unconjugated E4 at all time points over a 24 hour interval in the sc and po dosing experiments.

Example 7

Established competitive steroid binding assays were used to determine the relative binding affinity of estetrol (E4), as compared to 17α-ethinylestradiol(EE) and 17β-estradiol (E2), to human Estrogen Receptor (ER) α- and β-forms.

The method employed was adapted from the scientific literature and described in detail by Osbourn et al. (1993, Biochemistry, 32, 6229-6236). Recombinant human ERα and ERβ proteins were purified from transfected Sf9-cells. The iin vitro assays involved the use of either ERα or ERβ proteins and [$^3$H]E2, at a fixed concentration of 0.5 nM, as the labeled ligand. Recombinant human ERα or ERβ proteins were dissolved in binding buffer (10 mM Tris-HCL, pH 7.5, 10% glycerol, 1 mM DTT, 1 mg/ml BSA) and duplicate aliquots were then incubated with [$^3$H]E2 at a final concentration of 0.5 nM, together with a vehicle control (0.4% DMSO), or the same amount of vehicle containing increasing concentrations of unlabeled steroid ligands as competitors. After incubation for 2 h at 25° C., the unbound ligands were removed and the amounts of [$^3$H]E2 bound to either ERα or ERβ proteins were measured. The average amounts of [$^3$H]E2 bound to either ERα or ERβ proteins at each concentration of competitor were used to make inhibition curves. IC50 values were subsequently determined by a non-linear, least squares regression analysis. Inhibition constants (Ki) were calculated using the equation of Cheng and Prusoff (Cheng et al., 1973, Biochem. Pharmacol., 22, 3099-3108), using the measured IC50 of the tested compounds, the concentration of radioligand employed in the assay, and the historical values for the Kd of the radioligand, which were established as 0.2 nM and 0.13 nM for ERα and ERβ, respectively.

TABLE 6

Percent inhibition of specific binding to ERα and ERβ proteins using E4 as unlabeled steroid ligand and 0.5 nM [3H] as labeled competitor. Results of three separate experiments are shown.

| E4 final concentration | Percent inhibition of specific binding in | | | | | |
|---|---|---|---|---|---|---|
| | ERα steroid binding assay | | | ERβ steroid binding assay | | |
| | Test 1 | Test 2 | Test 3 | Test 1 | Test 2 | Test 3 |
| 1 μM | 98 | nd | nd | 87 | 90 | 95 |
| 0.3 μM | 92 | 94 | 101 | 74 | 74 | 77 |
| 0.1 μM | 83 | 85 | 86 | 56 | 54 | 50 |
| 0.03 μM | 64 | 66 | 63 | 19 | 25 | 30 |
| 10 nM | 43 | 32 | 28 | nd | nd | nd |
| 3 nm | 26 | 17 | 11 | nd | nd | nd | nd: not determined

TABLE 7

Experimentally determined inhibition constants (Ki) for estetrol (E4), 17α-ethinylestradiol (EE) and 17β-estradiol (E2), to human ERα and ERβ proteins. Relative preference for binding to ERα protein is also shown.

| Steroid ligands | Ki ERα (nM) | Ki ERβ (nM) | Relative ERα/ERβ preference(%) |
|---|---|---|---|
| EE | 0.23 | 0.025 | 11 |
| E2 | 0.21 | 0.015 | 7 |
| E4 | 4.9 | 19 | 400 |

Biochemtical assay results for E4 are presented as the percent inhibition of specific binding in three separate experiments (Table 6). For comparison of binding affinities of E4, EE and E2 to human ERα and ERβ proteins, experimentally observed Ki values are shown in Table 7. As compared to EE and E2, E4 demonstrates a unique binding profile with a strong preference (400%) for binding to the ERα protein (Table 7). In contrast, Ki values for ERβ protein are more pronounced for EE and E2 steroid ligands (Table 7).

Example 8

An established competitive steroid-binding assay (Hammond and Lahteenmaki. 1983. Clin Chem Acta 132:101-110) was used to determine the relative binding affinity of estetrol (E4), 17α-ethinylestradiol(EE2), 17β-estradiol (E2), testosterone (T)and 5α-dihydrotestosterone (DHT) for human sex Hormone Binding Globulin (SHBG).

Human SHBG was purified from transgenic mouse serum, as described previously (Awakumov GV et al., 2000. J Biol Chem 275: 25920-25925). The human SHBG prepared in this way was assessed to be >99% pure by polyacrylamide gel electrophoresis under denaturing conditions. Its steroid-binding characteristics are indistinguishable from SHBG in human serum (Awakumov GV et al., 2000. J Biol Chem 275: 25920-25925). The in vitro assay involved the use of the purified human SHBG and [$^3$H]DHT or [$^3$H]estradiol as labeled ligands. Human SHBG was treated for 30 min at room temperature with a dextran-coated charcoal (DCC) suspension in phosphate buffered saline (PBS) to remove any steroid ligand. After centrifugation (2,000×g for 10 min) to sediment the DCC, the supernatant containing the human SHBG was diluted in PBS to a concentration of 1 nM based on its steroid binding capacity.

Duplicate aliquots (100μl) of this human SHBG solution were then incubated with an equal volume of either [$^3$H]DHT or [$^3$H]estradiol at 10 nM, together with 100 μl of PBS alone or the same amount of PBS containing increasing concentrations of unlabeled steroid ligands as competitors in polystyrene test tubes. After incubation for 1 h at room temperature the. reaction mixtures were placed in an ice bath for a further 15 muin. Aliquots (600 μl) of an ice cold suspension of DCC were then added to each tube, and after a brief 2 seconds mixing, each tube was incubated in an ice bath for either 10 min or 5 min depending on whether [$^3$H]DHT or [$^3$H]estradiol were being used as labeled ligands, respectively. The unbound ligands adsorbed to DCC were then removed by centrifugation (2,000×g for 15 min at 4 C.), and the amounts of [$^3$H]labeled ligands bound to SHBG were counted in 2 ml ACS scintillation cocktail using in liquid scintillation spectrophotometer. The average amounts of [$^3$H]labeled ligands bound to SHBG at each concentration of competitor (B) were expressed as a percentage of the average amounts of [$^3$H]

labeled ligands bound to SHBG in the absence of competitor ($B_0$), and were plotted against the concentration of competitor in each assay tube.

Figure 6:
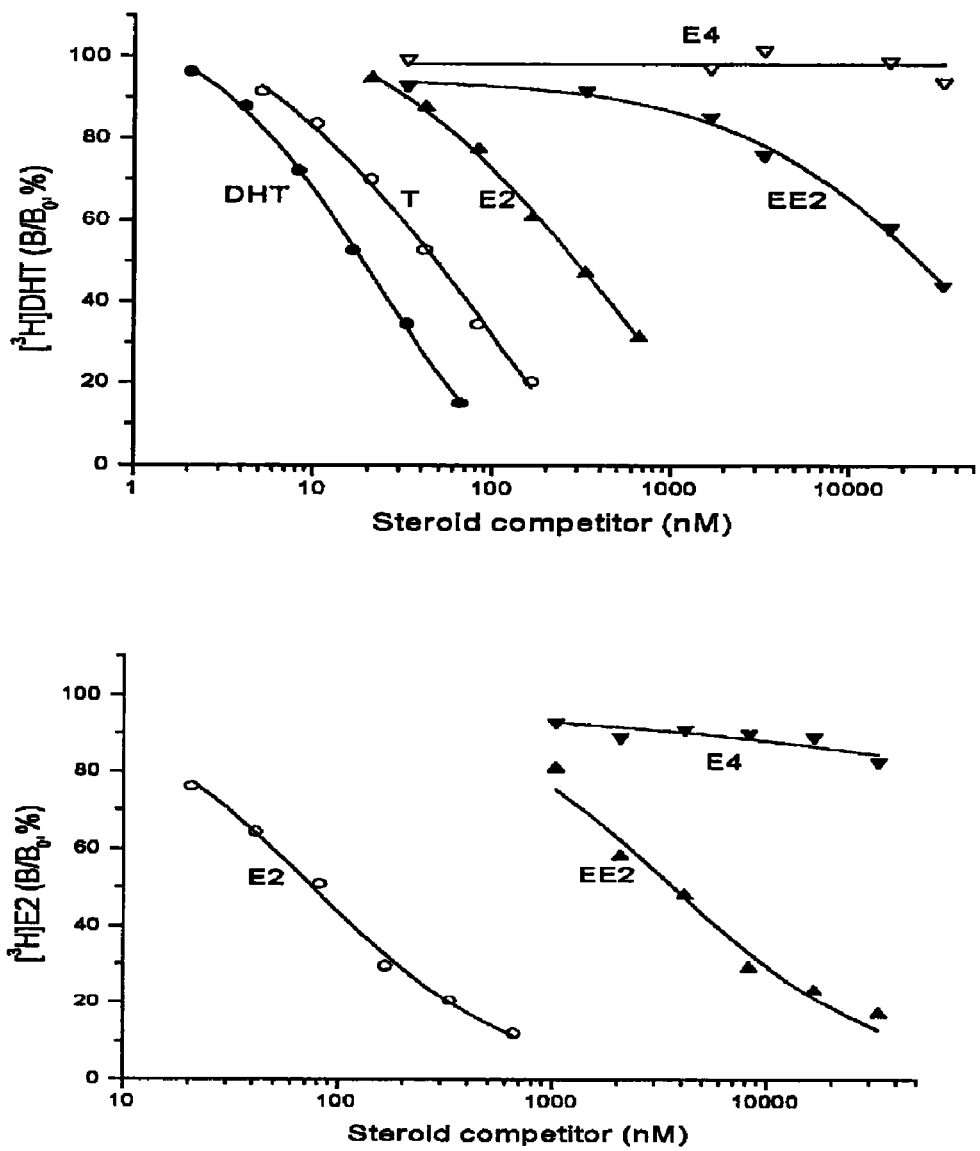
FIG. 6 is a graph showing the competitive displacement of [$^3$H]DHT (panel A) and [$^3$H]estradiol (panel B) from the human sex hormone-binding globulin steroid binding site. The unlabeled steroid ligands used as competitors were as follows: estetrol (E4), 17α-ethinylestradiol (EE2), 17β-estradiol (E2), testosterone (T) and 5α-dihydrotestosterone (DHT).

The results of the competitive binding assays are depicted in FIG. 6. As is clearly apparent from these competitive binding assays, estetrol does not bind at all to human SHBG when tested with either [$^3$H]DHT or [$^3$H]estradiol as labeled ligands. This is in marked contrast with reference steroids ethinylestradiol, 17β-estradiol, testosterone and 5α-dihydrotestosterone, which, in this order, show an increased relative binding affinity for human SHBG. Importantly, estetrol binding to SHBG was negligible when compared with the other estrogens tested, ethinylestradiol and 17β-estradiol.

Example 9

Dosage Units for Oral Administrations

The present estrogenic components may suitably be processed, together with additives, excipients and/or flavouring agents customary in galenic pharmacy, in accordance with the coniventional methods into the usual forms of administration. For oral administration, suitable are, in particular, tablets, dragees, capsules, pills, suspensions, or solutions.

Estetrol tablets: 1,000 tablets of 185 mg, containing 1.5 mg estetrol, are produced from the following formulation:

| | |
|---|---|
| Estetrol | 1.500 g |
| Polyvinylpyrrolidone (Kollidon 25 ® ex BASF) | 13.500 g |
| Lactose | 135.795 g |
| Microcrystalline cellulose (Avicel PH 101 ®) | 26.250 g |
| Glyceryl palmitostearate (Precirol ®) | 2.775 g |
| Anhydrous colloidal silica (Aerosil 200 ®) | 1.000 g |
| Crospovidone (Polyplasdone XL ®) | 4.000 g |
| Coloring agent | 0.180 g |

Example 10

Drug Delivery System for Transdermal Administration

Suitable formulations for the transdermal administration of estrogens are known in the art, and may be employed in the methods of the present invention. For example, suitable transdermal patch formulations for the administration of exogenous estrogen are described in U.S. Pat. No. 4,460,372 (Campbell et al.), U.S. Pat. No. 4,573,996 (Kwiatek et al.), U.S. Pat. No. 4,624,665 (Nuwayser), U.S. Pat. No. 4,722,941 (Eckert et al.), U.S. Pat. No. 5,223,261 (Nelson et al.), the disclosures of which are hereby incorporated by reference.

One suitable type of transdermal patch for use in the methods of the present invention includes a backing layer which is non-permeable, a permeable surface layer, an adhesive layer substantially continuously coating the permeable surface layer, and a reservoir located or sandwiched between the backing layer and the permeable surface layer such that the backing layer extends around the sides of the reservoir and is joined to the permeable surface layer at the edges of the permeable surface layer. The reservoir contains the estrogenic component and is in fluid contact with the permeable surface layer. The transdermal patch is adhered to the skin by the adhesive layer on the permeable surface layer, such that the permeable surface layer is in substantially continuous contact with the skin when the transdermal patch is adhered to the skin.

While the transdermal patch is adhered to the skin of the subject, the estrogenic component contained in the reservoir of the transdermal patch is transferred via the permeable surface layer, through the adhesive layer, and to and through the skin of the subject. The transdermal patch may suitably include one or more penetration-enhancing agents in the reservoir that enhance the penetration of the estrogenic component through the skin.

Examples of suitable materials which may comprise the backing layer are well known in the art of transdermal patch delivery, and any conventional backing layer material may be employed in the transdermal patch of the instant invention. Specific examples of suitable backing layer materials include but are not limited to polyester film, such as high density polyethylene, low density polyethylene or composites of polyethylene; polypropylene; polyvinyl chloride, polyvinylidene chloride; ethylene-vinyl acetate copolymers; and the like.

Examples of suitable permeable surface layer materials are also well known in the art of transdermal patch delivery, and any conventional material which is permeable to the estrogenic component, may be employed in the transdermal patch of the instant invention. Specific examples of suitable materials for the permeable surface layer include but are not limited to dense or microporous polymer films such as those comprised of polycarbonates, polyvinyl chlorides, polyamides, modacrylic copolymers, polysulfones, halogenated polymers, polychloroethers, acetal polymers, acrylic resins, and the like. Specific examples of these types of conventional permeable membrane materials are described in U.S. Pat. No. 3,797,494 to Zaffaroni.

Examples of suitable adhesives which may be coated on the backing layer to provide the adhesive layer are also well known in the art and include, for example pressure sensitive adhesives such as those comprising acrylic and/or methacrylic polymers. Specific examples of suitable adhesives include polymers of esters of acrylic or methacrylic acid (e.g., n-butanol, n-pentanol, isopentanol, 2-methyl butanol, 1-methyl butanol, 1-methyl pentanol, 3-methyl pentanol, 3-methyl pentanol, 3-ethyl butanol, isooctanol, n-decanol, or n-dodecanol esters thereof) alone or copolymerized with ethylenically unsaturated monomers such as acrylic acid, methacrylic acid, acrylamide, methacrylamide, N-alkoxymethyl acrylamides, N-alkoxymethyl methacrylamides, N-t-butylacrylamide, itaconic acid, vinyl acetate, N-branched C.sub.10-24 alkyl maleamic acids, glycol diacrylate, or mixtures of the foregoing; natural or synthetic rubbers such as silicon rubber, styrene-butadiene rubber, butyl-ether rubber, neoprene rubber, nitrile rubber, polyisobutylene, polybutadiene, and polyisoprene; polyurethane elastomers; vinyl polymers such as polyvinyl alcohol, polyvinyl ethers, polyvinyl pyrrolidone, and polyvinyl acetate; ureaformaldehyde resins; phenol formaldehyde resins; resorcinol formaldehyde resins; cellulose derivatives such as ethyl cellulose, methyl cellulose, nitrocellulose, cellulose acetatebutyrate, and carboxymethyl cellulose; and natural gums such as guar, acacia, pectin, starch, destria, gelatin, casein, etc.

As will be apparent to those skilled in the art, the adhesive layer should be inert to the estrogenic component, and should not interfere with the transdermal delivery of the estrogenic component through the permeable surface layer. Pressure sensitive adhesives are preferred for the adhesive layer of the transdermal patch to facilitate the application of the patch to the skin of the subject.

Suitable penetration-enhancing agents are well known in the art as well. Examples of conventional penetration-enhancing agents include allkanols such as ethanol, hexanol, cyclohexanol, and the like; hydrocarbons such as hexane, cyclohexane, isopropylbenzene; aldehydes and ketones such as cyclohexanone, acetamide; N,N-di(lower alkyl)acetamides such as N,N-diethylacetamide, N,N-dimethyl acetamide; N-(2-hydroxyethyl)acetamide; esters such as N,N-di-lower alkyl sulfoxides; essential oils such as propylene glycol, glycerine, glycerol monolaurate, isopropyl myristate, and ethyl oleate; salicylates; and mixtures of any of the above.

In another example of a transdermal patch which is suitable for the transdermal delivery of the estrogenic component according to the present invention, said estrogenic component is incorporated into the adhesive layer rather than being contained in a reservoir. Examples of these types of patches are conventionally known and include, for example, the CLIMERA.®. patch available from Berlex. This type of transdermal patch comprises a backing layer and an adhesive/drug layer. The adhesive/drug layer has the combined function of adhering the patch to the skin of the subject and containing the estrogenic component, which is to be administered. The active ingredient is leached from the adhesive/drug layer to and through the skin of the subject when the patch is adhered to the skin.

Any of the backing layers described herein above may be employed in this embodiment as well. In addition, any of the suitable adhesives described above may be employed. The adhesive/drug layer comprises a relatively homogeneous mixture of the selected adhesive and the active ingredient. Typically, the adhesive/drug layer comprises a coating substantially covering one surface of the backing layer. The adhesive/drug layer may also include a penetration enhancing agent such as those described above by incorporating the penetration enhancing agent into the substantially homogeneous mixture of the adhesive and the active ingredient.

As will be readily apparent to those skilled in the art, the transdermal patches according to the present invention may include a variety of additional excipients which are conventionally employed to facilitate the transdermal administration of the estrogenic component. Examples of such excipients include but are not limited to carriers, gelling agents, suspending agents, dispersing agents, preservatives, stabilisers, wetting agents, emulsifying agents, and the like. Specific examples of each of these types of excipients are well known in the art and any conventional excipients may be employed in the transdermal patches of the instant invention.

The amount of estrogenic component contained in the transdermal patch formulations will depend upon the precise form of estrogenic component to be administered, but should be sufficient to deliver at least 20 μg per day. Typically, the transdermal patches are designed to be worn for several days before replacement is required. Thus the amount of estrogenic component in the patch must be sufficient to permit the administration of at least 20 μg per day for a period of several days. As an example, a transdermal patch according to the present invention which is designed to administer around 200 μg of estetrol per day for seven (7) days would contain approximately 20 mg of the estrogen. Based upon this information, one skilled in the art would be able to establish the necessary amount of estrogenic component to be included in a given transdermal patch to achieve the delivery of the correct daily dose of estrogenic component.

Example 11

Drug Delivery System for Intranasal Administration

Suitable nontoxic pharmaceutically acceptable carriers for use in a drug delivery system for intranasal administration of the present estogenic component will be apparent to those skilled in the art of nasal pharmaceutical formulations. For those not skilled in the art, reference is made to "Remington's Pharmaceutical Sciences", 4th edition, 1970. Obviously, the choice of suitable carriers will depend on the exact nature of the particular nasal dosage form desired, e.g. whether the estrogenic component is to be formulated into a nasal solution (for use as drops or as a spray), nasal microspheres, a nasal suspension, a nasal ointment or a nasal gel, as well as on the identity of the estrogenic component.

Examples of the preparation of typical nasal compositions are set forth below.

Nasal Solution:
  5 mg of estetrol is combined with 10 mg of Tween 80. That mixture is then combined with a quantity of isotonic saline sufficient to bring the total volume to 50 ml. The solution is sterilised by being passed through a 0.2 micron Millipore filter.

Nasal Gel:
  250 ml of isotonic saline are heated to 80° C. and 1.5 g of Methocel are added, with stirring. The resultant mixture is allowed to stand at room temperature for 2 hours. Then, 10 mg of estetrol are mixed together with 10 mg of Tween 80. The estetrol/Tween mixture and a quantity of isotonic saline sufficient to bring the total volume to 500 ml were added to the gel and thoroughly rixed.

Example 12

Drug Delivery System for Intravaginal Administration

The intravaginal drug delivery vehicle may suitably take the form of a vaginal ring. Vaginal rings are torous shaped devices designed to deliver a relatively constant dose of drug to the vagina usually over a period of weeks to months. Typically, they are made of a poly EVA elastomer and the estrogenic component is released by diffusion though the elastomer. The vaginal ring is designed to regulate the release rate of the estrogenic component so as to provide the user with the appropriate daily dose. Among the important factors governing release are the solubility of the estrogenic component in the ring elastomer, the surface area of the drug reservoir, the distance the drug must diffuse through the ring body to reach its surface and the molecular weight of the drug.

If relatively high release rates are desired, they can be attained by a drug load at the ring surface as is characteristic of the homogeneous matrix ring design. This design, however, suffers from rapidly declining release rates as the distance the drug must travel to reach the ring surface increases as the drug load near the surface is depleted. If moderately high release rates are needed to provide the appropriate dose, a design which modulates release rate by imposing a layer of drug-free elastomer between the drug reservoir and the ring exterior is appropriate. This may be attained by coating a homogeneous ring, or to conserve drug, by incorporating a drug-free core, a shell design may be used. If an even lower release rate is desired, the drug may be confined to a small diameter at the center of the ring ("core ring"). Numerous types of vaginal rings have been described in the patent and non-patent literature alike.

An example of the preparation of an estetrol containing intravaginal ring is set forth below:

Four 58 mm core rings are prepared as follows. Fifty grams of Silastic 382® are mixed with 0.3 g of stannous octoate, transferred to a 50 cc plastic syringe and injected into four brass ring moulds. After 45 minutes, the moulds are opened, the rings removed, the flash is trimmed and the rings are cut open at a 45° angle. A mixture of 84.4 g Silastic 382®, 36.6 g of micronised estetrol are mixed in a Teflon bowl. The mixture is transferred to a Lucite coating cup with a bottom opening of 8.7 mm. The open rings are heated at 110° C. for 30 minutes, cooled and weighed. The open rings weigh approximately 9.8 g. The open rings are pulled through the coating cup and dipped in a solution of 0.67% stannous octoate in toluene (w/v). The open ring is again heated at 110° C. for 30 minutes and reweighed. The weight of the coated open ring is approximately 10.3 g and the weight of the coating on the open rings is therefore approximately 0.5 g.

In order to apply the outer layer a 16.5 cm long piece of silicone rubber tubing having 6.3 mm diameter and 0.3 mm wall thickness is swollen in hexane and the open ring coated with the medicated layer is placed inside the silicone rubber tubing. The hexane is evaporated at room temperature and the tubing contracted to the size of the open ring forming an outer layer having a thickness of 0.2 mm.

The excess tubing.is trimmed flush with the ends of the open ring and Dow Corning Medical Adhesive A is applied at both ends of the open ring and to 1 cm of the outer layer at both ends of the open ring. A 4 cm piece of silicone tubing 6.3 mm inner diameter and 0.3 mm wall thickness is swollen with hexane and placed over the two ends of the open ring to close the ring. The ring is held for about two minutes until the tubing has shrunk and fits snugly over the ring junction. The adhesive is allowed to cure for 24 hours, the rings are rinsed in alcohol and air dried.

Example 13

Depot Formulation for Intramuscular Administration

An estetrol containing depot formulation can suitably be prepared as set forth below.

At room temperature, 1000 mg estetrol is dispersed in 6 millilitre dehydrated ethanol. This solution is then diluted with 660 ml arachidis oil under thorough stirring. The resulting solution is sterilised by filtration.

In case an estetrol ester is used, e.g. estetrol valerate esters, a significantly lower release rate can be obtained. Such low release rates are particularly advantage if the depot injections are to be administered at relatively long time intervals, e.g. intervals of more than 1 week.

The invention claimed is:

1. A method of hormone replacement therapy, comprising administering to a person in need of such a therapy an effective amount of an estrogenic component selected from the group consisting of:
substances represented by the following formula

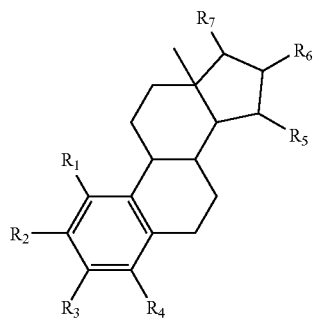

in which formula $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; and no more than 3 of $R_1$, $R_2$, $R_3$, $R_4$ are hydrogen atoms;
derivatives of these substances wherein the hydrogen atom of at least one of the hydroxyl groups in said formula has been substituted by an acyl radical of a hydrocarbon carboxylic, sulfonic or sulfamic acid of 1-25 carbon atoms; tetrahydrofuranyl; tetrahydropyranal; or a straight or branched chain glycosidic residue containing 1-20 glycosidic units per residues; and mixtures thereof,
said composition containing virtually no progestogen, anti-progestin or gonadotropin releasing hormone wherein said method does not comprise administering progestogen, anti-progestin or gonadotropin releasing hormone.

2. The method according to claim 1, wherein the method comprises administering the estrogenic component in an effective amount to treat symptoms of or reduce the risk of developing hypoestrogenism that are selected from the group consisting of osteoporosis, arteriosclerosis, climacteric symptoms.

3. The method according to claim 2, wherein at least 2 of the groups $R_1$, $R_2$, $R_3$ and $R_4$ represent a hydrogen atom.

4. The method according to claim 2, wherein 3 of the groups $R_1$, $R_2$, $R_3$ and $R_4$ represent a hydrogen atom.

5. The method according to claim 2, wherein groups $R_1$, $R_2$ and $R_4$ represent hydrogen atoms.

6. The method according to claim 1, wherein the hormone replacement therapy is administered to treat (peri-)menopausal disorders, post-menopausal disorders, and/or hypoestrogenism resulting from hypogonadism, castration, primary ovarian failure, gonadotropin-releasing hormone analogue treatment or cancer treatment.

7. The method according to claim 1, wherein the method comprises daily administration of at least 0.001 mg of the estrogenic component.

8. The method according to claim 1, wherein the method comprises oral, transdermal, intranasal, intravaginal, rectal, pulmonary, buccal, subcutaneous or intra-uterine administration of the estrogenic component.

9. The method according to claim 8, wherein the method comprises oral or transdermal administration of the estrogenic component.

10. The method according to claim 9, wherein the method comprises oral administration of the estrogenic component.

11. The method according to claim 1, wherein the composition contains virtually no an antisense oligonucleotide that is complementary to a nucleotide sequence for follicle stimulating hormone receptor.

12. The method according to claim 1, wherein the estrogenic component is administered in an amount effective to achieve a blood serum concentration of at least 1 nanogram per liter.

13. The method according to claim 1, wherein the estrogenic component is administered in an amount effective to achieve a blood serum concentration of at least 10 nanograms per liter.

14. The method according to claim 1, wherein the estrogenic component is administered in an amount of at least 1 µg per kg of bodyweight per day.

15. The method according to claim 1, wherein the estrogenic component is administered in an amount of at least 5 µg per kg of bodyweight per day.

16. The method according to claim 1, wherein the method comprises administering the estrogenic component for a period of at least 1 month.

17. The method according to claim 1, wherein the method comprises administering the estrogenic compound for a period of at least 3 months.

18. The method according to claim 1, wherein the composition contains no progestogen or anti-progestogen.

19. The method according to claim 1, wherein the method is administered to individuals who have not been oophorectomized, or in whom the risk of endometrial stimulation by estrogenic compositions is not minimized or absent.

20. The method according to claim 1, wherein the method does not employ a slow release formulation.

21. A drug delivery system for enteral or parenteral administration containing the estrogenic component as defined in claim 1, said drug delivery system being selected from the group consisting of solid oral dosage units, semi-solid oral dosage units, patches, gels, tapes, creams, tablets, suppoitories and pessaries, wherein the system contains at least 1 µg of the estrogenic component and virtually no progestogen, anti-progestogen or gonadotropin releaing hormone.

22. The drug delivery system according to claim 21, wherein the drug delivery system is a solid or semi-solid oral dosage unit.

23. The method according to claim 2, wherein the effective amount is to treat symptoms of hypoestrogenism.

24. A method of hormone replacement therapy, comprising orally administering to a person in need of such a therapy an effective amount of an estrogenic component selected from the group consisting of:
substances represented by the following formula

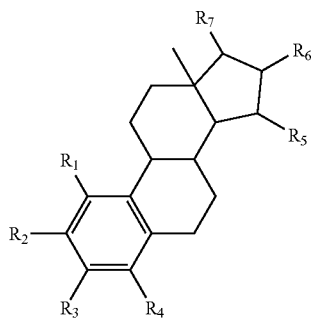

in which formula $R_1$, $R_2$, $R_3$, $R_4$ independently are a hydrogen atom, a hydroxyl group or an alkoxy group with 1-5 carbon atoms; each of $R_5$, $R_6$, $R_7$ is a hydroxyl group; and no more than 3 of $R_1$, $R_2$, $R_3$, $R_4$ are hydrogen atoms;
   derivatives of these substances wherein the hydrogen atom of at least one of the hydroxyl groups in said formula has been substituted by an acyl radical of a hydrocarbon carboxylic, sulfonic or sulfamic acid of 1-25 carbon atoms; tetrahydrofuranyl; tetrahydropyranal; or a straight or branched chain glycosidic residue containing 1-20 glycosidic units per residues; and mixtures thereof,
   said composition containing virtually no progestogen or anti-progestin or gonadotropin releasing hormone; wherein said method does not comprise administering progestogen, anti-progestin or gonadotropin releasing hormone.

25. The method according to claim 24, wherein the method comprises administering the estrogenic component in an effective amount to treat symptoms of or reduce the risk of developing hypoestrogenism that are selected from the group consisting of osteoporosis, arteriosclerosis and climacteric symptoms.

26. The method according to claim 25, wherein at least 2 of the groups $R_1$, $R_2$, $R_3$ and $R_4$ represent a hydrogen atom.

27. The method according to claim 25, wherein 3 of the groups $R_1$, $R_2$, $R_3$ and $R_4$ represent a hydrogen atom.

28. The method according to claim 25, wherein groups $R_1$, $R_2$ and $R_4$ represent hydrogen atoms.

29. The method according to claim 24, wherein the hormone replacement therapy is administered to treat (peri-)menopausal disorders, post-menopausal disorders, and/or hypoestrogenism resulting from hypogonadism, castration, primary ovarian failure, gonadotropin-releasing hormone analogue treatment or cancer treatment.

30. The method according to claim 24, wherein the method comprises daily administration of at least 0.001 mg of the estrogenic component.

31. The method according to claim 24, wherein the composition contains virtually no gonadotropin hormone releasing hormone analogue or luteinizing hormone releasing hormone or an antisense oligonucleotide that is complementary to the nucleotide sequence of the follicle stimulating hormone receptor.

32. The method according to claim 24, wherein the estrogenic component is administered in an amount effective to achieve a blood serum concentration of at least 1 nanogram per liter.

33. The method according to claim 24, wherein the estrogenic component is administered in an amount effective to achieve a blood serum concentration of at least 10 nanograms per liter.

34. The method according to claim 24, wherein the estrogenic component is administered in an amount of at least 1 µg per kg of bodyweight per day.

35. The method according to claim 24, wherein the estrogenic component is administered in an amount of at least 5 µg per kg of bodyweight per day.

36. The method according to claim 24, wherein the method comprises administering the estrogenic component for a period of at least 1 month.

37. The method according to claim 24, wherein the method comprises administering the estrogenic compound for a period of at least 3 months.

38. The method according to claim 24, wherein the composition contains no progestogen or anti-progestogen.

39. The method according to claim 24, wherein the method is administered to individuals who have not been oophorectomized, or in whom the risk of endometrial stimulation by estrogenic compositions is not minimized or absent.

40. The method according to claim 24, wherein the method does not employ a slow release formulation.

* * * * *